United States Patent [19]

Perlin

[11] Patent Number: 5,622,823

[45] Date of Patent: Apr. 22, 1997

[54] SYSTEM AND METHOD FOR PRODUCING MAPS AND CLONING GENES THEREFROM

[76] Inventor: Mark W. Perlin, 5904 Beacon St., Pittsburgh, Pa. 15217

[21] Appl. No.: 323,532

[22] Filed: Oct. 14, 1994

Related U.S. Application Data

[63] Continuation of Ser. No. 105,753, Aug. 12, 1993, abandoned.

[51] Int. Cl.⁶ .............................. C12N 15/10; C12Q 1/68
[52] U.S. Cl. .............................................. 435/6; 435/172.3
[58] Field of Search ........................................ 435/6, 172.3

[56] References Cited

PUBLICATIONS

Cox et al. (1990), Science 250: 245–250.
Mott et al. (1993) Nucleic Acids Research, vol. 21, pp. 1965–1974.
Green et al. (1991) PCR Methods and Applications, vol. 1, pp. 77–90.
Wilson (1992) Cytogenetics and Cell Genetics, vol. 59, pp. 110–111.
Monaco et al. (1991) Nucleic Acids Research, vol. 19, pp. 3315–3318.
Sambrook et al. (1989) Molecular Cloning: A Laboratory Manual (Cold Spring HarborLab, Cold Spring Harbor) pp. 9.1–9.62.
Altherr et al. (1992) Genomics, vol. 13, pp. 1040–1046.

Primary Examiner—David Guzo
Assistant Examiner—Philip W. Carter
Attorney, Agent, or Firm—Ansel M. Schwartz

[57] ABSTRACT

The present invention pertains to a process for efficiently and accurately constructing indirectly high-resolution maps of genomes and other entities. Specifically, the process comprises the steps of generating three sets of reagents, namely, (1) sample points, (2) covering regions, and (3) probes; performing parallel experiments to efficiently compare these reagents and acquire two data tables, one of (a) probes with covering regions, and another of (b) covering regions with sample points; combining these two independent tables by means of an inner product operation to produce a third table that indirectly compares probes with sample points; analyzing this computed table to construct a high-resolution map of the probes, the sample points, and the covering regions. The resulting integrated map is then used to efficiently search for probes based on their proximity to selected sample points. With genome maps, this search can enable the rapid discovery of genes, their products, and their useful applications.

27 Claims, 9 Drawing Sheets

SYSTEM AND METHOD FOR PRODUCING MAPS AND CLONING GENES THEREFROM

This is a continuation of application Ser. No. 08/105,753 filed on Aug. 12, 1993, now abandoned.

FIELD OF THE INVENTION

The present invention is related to a process for efficiently and accurately constructing high-resolution maps of genomes and other entities. More specifically, the present invention is related to an indirect mapping process that takes two efficiently obtainable data tables, and computationally combines them into a third table, from which an indirect high-resolution map can be constructed.

BACKGROUND OF THE INVENTION

For the positional cloning of genes and other novel types of genetic experiments, in humans and other organisms, there is a crucial need for techniques that can rapidly construct genome-wide high-resolution ordered clone maps. Current best methods, such as sequence-tagged site (STS) content mapping, entail a large number of experiments, and, in practice, require large low-resolution yeast artificial chromosome (YAC) clones and very many STSs. Here, Inner Product Mapping (IPM) is introduced that overcomes these limitations. IPM uses radiation hybrids (RHs) to provide localizing signatures for YACs. Two independent data tables are obtained which compare YACs against RHs, and RHs against STSs; these tables are combined to produce a computed map of the YACs against ordered STSs. IPM maps each YAC independently, requires relatively few RH comparisons to map a YAC, and can work with small (or large) YACs and few (or many) STSs.

There is currently considerable effort directed toward constructing genetic and physical genome maps for humans and model organisms. By localizing a phenotype on the genetic map, the corresponding physical and ordered clone maps can be used to retrieve chromosomal segments containing a gene of interest. DNA sequencing of these segments can determine the gene's DNA sequence, thus enabling functional studies of the gene's product and its mutations. A genetic map currently exists at 5 centiMorgan (cM) resolution (NIH/CEPH Collaborative Mapping Group (1992). A Comprehensive Genetic Linkage Map of the Human Genome. *Science*, 258: 67–86; Weissenbach, J., Gyapay, G., Dib, C., Vignal, A., Morissette, J., Millasseau, P., Vaysseix, G., and Lathrop, M. (1992). A second generation linkage map of the human genome. *Nature*, 359: 794–801), and a greater resolution map is currently being developed. Physical and ordered clone mapping of chromosomes, however, is still in its infancy (Maier, E., Hoheisel, J. D., McCarthy, L., Mott, R., Grigoriev, A. V., Monaco, A., Larin, Z., and Lehrach, H. (1992). Complete coverage of the *Schizosaccharomyces pombe* genome in yeast artificial chromosomes. *Nature Genetics*, 1: 273–277). Current technologies are enabling the construction of a 1 megabase (mb) resolution map (Bellanne-Chantelot, C., Lacroix, B., Ougen, P., Billault, A., Beaufils, S., Bertrand, S., Georges, S., Glibert, F., Gros, I., Lucotte, G., Susini, L., Codani, J.-J., Gesnouin, P., Pook, S., Vaysseix, G., Lu-Kuo, J., Ried, T., Ward, D., Chumakov, I., Le Paslier, D., Barillot, E., and Cohen, D. (1992). Mapping the Whole Genome by Fingerprinting Yeast Artificial Chromosome. *Cell*, 70: 1059–1068), but require tremendous experimental effort (Green, E. D., and Green, P. (1991). Sequence-tagged site (STS) content mapping of human chromosomes: theoretical considerations and early experiences. *PCR Methods and Applications*, 1: 77–90). For routine use, a higher resolution 250 kilobase (kb) map would be far more useful for locating genes. There is, therefore, a great and immediate need for ordered clone mapping strategies that are both more efficient and achieve higher resolution.

Crucial to the success of large scale mapping experiments is the availability of numerous sequence tagged sites (Olson, M., Hood, L., Cantor, C., and Botstein, D. (1989). A common language for physical mapping of the human genome. *Science*, 245: 1434–35) (STSs), which are unique, very short 100–500 base pair (bp) genomic sequences that can be amplified from sample DNA by the polymerase chain reaction (PCR). Polymorphic STS markers have proved highly successful in genetic linkage map construction (Weissenbach, J., Gyapay, G., Dib, C., Vignal, A., Morissette, J., Millasseau, P., Vaysseix, G., and Lathrop, M. (1992). A second generation linkage map of the human genome. *Nature*, 359: 794–801). Further, when also used as physical mapping reagents, these STSs can correlate the genetic and physical maps.

High resolution (<250 kb) physical maps of STSs can be efficiently constructed via radiation hybrid (RH) mapping (Cox, D. R., Burmeister, M., Price, E. R., Kim, S., and Myers, R. M. (1990). Radiation hybrid mapping: a somatic cell genetic method for constructing high-resolution maps of mammalian chromosomes. *Science*, 250: 245–250). A RH clone contains several very large (5 to 50 mb), nonoverlapping human chromosome fragments from a specific chromosome in a rodent cell line. These chromosome fragments are randomly formed, and cover 25–50% of the chromosome. To physically map STSs, a data table is constructed which compares a set of RH clones against a set of unordered STSs. Each entry in the table records whether or not an STS is present in some fragment of a RH. By permuting the order of the STSs (i.e., the table's columns) (Chakravarti, A., and Reefer, J. E. (1992). A Theory for Radiation Hybrid (Goss-Harris) Mapping: Application to Proximal 21q Markers. In Genetic Analysis Workshop 7: Issues in Gene Mapping and the Detection of Major Genes. Cytogenet Cell Genet, 99–101. vol. 59, (MacCluer, J. W., Chakravarti, A., Cox, D., Bishop, D. T., Bale, S. J., and Skolnick, M. H., eds.; Cox, D. R., Burmeister, M., Price, E. R., Kim, S., and Myers, R. M. (1990). Radiation hybrid mapping: a somatic cell genetic method for constructing high-resolution maps of mammalian chromosomes. *Science*, 250: 245–250), an ordering can be found either by minimizing the number of obligate breaks (Boehnke, M. (1992). Radiation hybrid mapping by minimization of the number of obligate chromosome breaks. In Genetic Analysis Workshop 7: Issues in Gene Mapping and the Detection of Major Genes. Cytogenet Cell Genet, 96–98. vol. 59, (MacCluer, J. W., Chakravarti, A., Cox, D., Bishop, D. T., Bale, S. J., and Skolnick, M. H., eds.; Weeks, D. E., Lehner, T., and Ott, J. (1992). Preliminary ranking procedures for multilocus ordering based on radiation hybrid data. In Genetic Analysis Workshop 7: Issues in Gene Mapping and the Detection of Major Genes. Cytogenet Cell Genet, 125–127. vol. 59, (MacCluer, J. W., Chakravarti, A., Cox, D., Bishop, D. T., Bale, S. J., and Skolnick, M. H., eds.)) present in all RH rows, or by using maximum likelihood methods (Chakravarti et al., 1992; Cox, D. R., Burmeister, M., Price, E. R., Kim, S., and Myers, R. M. (1990). Radiation hybrid mapping: a somatic cell genetic method for constructing high-resolution maps of mammalian chromosomes. *Science*, 250: 245–250). Inter-STS distances can also be estimated (Boehnke, M., Lange, K., and Cox, D. R. (1991). Statistical Methods for Multipoint Radiation Hybrid Mapping. *Am. J. Hum. Genet.*, 49: 1174–1188; Chakravarti et al., 1992; Cox, D. R., Burmeister, M., price, E. R., Kim, S., and Myers, R. M. (1990). Radiation hybrid mapping: a somatic cell genetic method for constructing high-resolution maps of mammalian chromosomes. *Science*, 250: 245–250) by counting the RH breaks occurring between STSs.

Yeast artificial chromosome (YAC) clones (Bellanne-Chantelot et al., 1992; Burke, D. T., Carle, G. F., and Olson, M. V. (1987). Cloning of large exogenous DNA into yeast by means of artificial chromosomes. *Science*, 236: 806–812) can perpetuate a large (100 kb to 1.2 mb) linear sequence of human DNA. Since YAC DNA inserts are very large, an ordered YAC clone map is an ideal reagent for retrieving genes via positional cloning. Such YAC orderings can be constructed by labor and time intensive techniques such as hybridization fingerprinting, which compares restriction enzyme digests of two YACs at a time for commonalities in their fingerprint patterns, and extends contigs of overlapping YACs. The current best approach to ordering YACs is STS-content mapping (Green, E. D., and Green, P. (1991). Sequence-tagged site (STS) content mapping of human chromosomes: theoretical considerations and early experiences. *PCR Methods and Applications*, 1: 77–90), which employs YAC vs. STS comparisons. Two YACs overlap when they share a common STS; YACs containing two or more STSs can be used to extend contigs. When the STSs are genetically mapped, there is an immediate correspondence with the physical YAC clone map. The chief drawback to this method is that large YACs and very many STSs must be used to achieve sufficient intersections of YACs with STSs. Another likely candidate approach for mapping YACs at high resolution is RH mapping. Unfortunately, YAC inserts are too large to satisfy the necessary break minimization assumptions.

This invention utilizes Inner Product Mapping (IPM), a new technique that enables high resolution mapping of YACs using RHs. IPM employs a YAC vs. RH comparison data table, but supplements it with localizing information for each RH, specifying where its fragments reside on the chromosome: e.g., a RH vs. ordered STS table. When these two independent data tables are mathematically combined, a computed YAC vs. ordered STS table is obtained. The positive entries in this computed table localize the YAC along the chromosome or genome.

Lehrach's group has demonstrated the feasibility of performing highly parallelized experiments which can compare, for example, one RH against tens of thousands of gridded YACs in a singe experiment (Monaco, A. P., Lam, V. M. S., Zehetner, G., Lennon, G. G., Douglas, C., Nizetic, D., Goodfellow, P. N., and Lehrach, H. (1991). Mapping irradiation hybrids to cosmid and yeast artificial chromosome libraries by direct hybridization of Alu-PCR products. *Nucleic Acids Res*, 19(12): 3315–3318). This group has noted the utility of inner products, but has only used them for consistency checks, and not for building maps (Mott, R., Grigoriev, A., Maier, E., Hoheisel, J., and Lehrach, H. (1993). Algorithms and software tools for ordering clone libraries: application to the mapping of the genome of *Schizosaccharomyces pombe*. *Nucleic Acids Research*, 21(8): 1965–1974). Studies of the distribution of Alu and L-1 interspersed repetitive sequences (IRS) in YACs (Arveiler, B., and Porteous, D. J. (1992). Distribution of Alu and L1 repeats in human YAC recombinants. *Mammalian Genome*, 3: 661–668) and chromosomes have demonstrated the utility of using IRS-PCR as a mechanism for extracting human DNA content from various clonal reagents. Statistics for superimposing recombinant chromosomes in pedigrees have been used recently in genetic mapping (Nelson, S. F., McCusker, J. H., Sander, M. A., Kee, Y., Modrich, P., and Brown, P. O. (1993). Genomic mismatch scanning: a new approach to genetic linkage mapping. *Nature Genetics*, 4(May): 11–18; Ward, P. J. (1993). Some Developments on the Affected-Pedigree-Member Method of Linkage Analysis. *Am. J. Hum. Genet.*, 52: 1200–1215), but, unlike IPM, make no use of neighborhood information and have not been applied to constructing physical maps.

SUMMARY OF THE INVENTION

The present invention pertains to a method for producing a gene. The method comprises the steps of isolating a gene from a map constructed by using radiation hybrids versus probes. Then there is the step of producing the gene isolated from the map.

The present invention also pertains to a system for cloning a gene of a genome. The system comprises means for isolating a sufficiently large set of first DNA sequences having a size between 100 b–40 kb to achieve a desired resolution. Each first DNA sequence is part of the genome. The system is also comprised of means for isolating a sufficiently large set of second DNA sequences having a size between 40 kb–2 mb to achieve the desired resolution. Each second DNA sequence is part of the genome. Additionally, the system comprises means for isolating a sufficiently large set of collection of DNA sequence fragments wherein each fragment's average size is greater than or equal to the size of said second DNA sequence fragment to achieve the desired resolution. Each collection of DNA sequence fragments is part of the genome. The system comprises a computer having a memory and means for inputting information into the computer about the set of second DNA sequences, the set of first DNA sequences and the set of collections of DNA sequence fragments. There is means for forming a Table A in the memory. Table A determines the containment or overlap of the set of second DNA sequences against the set of collections of DNA sequence fragments. The system comprises means for forming a Table B in the memory. Table B determines the containment or overlap of the set of first DNA sequences against the set of collections of DNA sequence fragments. Additionally, the system comprises means for forming a Table L from Table A and Table B. Table L provides localization information about the set of second DNA sequences relative to the set of first DNA sequences. There is means for producing a map of the gene from Table L. The map determines where the set of first DNA sequences are located within the genome and where the set of second DNA sequences are located within the genome. The system also comprises means for producing a gene in the genome of the map. Preferably, there can also be means for purifying derivatives of the gene produced in the gene producing means, and the first DNA sequences are STSs, the set of second DNA sequences are YACs, and the DNA sequence fragments are radiation hybrids.

The present invention also pertains to a method for cloning a gene of a genome. The method comprises the steps of identifying a portion of a genome to be mapped. Then there is the step of setting a desired resolution of the map. Next, there is the step of isolating a sufficiently large set of first DNA sequences having a size between 100 b–40 kb to achieve the desired resolution. Each first DNA sequence is part of the genome. Then there is the step of isolating a sufficiently large set of second DNA sequences having a size between 40 kb–2 mb to achieve the desired resolution. Each second DNA sequence is part of the genome. Next there is the step of isolating a sufficiently large set of collections of DNA sequence fragments wherein each fragment's average size is greater than or equal to the size of each of said second DNA sequences to achieve the desired resolution. Each collection of DNA sequence fragments is part of the genome. Then there is the step of forming a Table A in a memory of a computer. The Table A determines the containment or overlap of a set of second DNA sequences against the collection of DNA sequence fragments. Next there is the step of forming a Table B in the memory wherein Table B determines the containment or overlap of a set of first DNA sequences against the collection of DNA sequence fragments. Next there is the step of operating a processor of the computer on Table A and Table B to produce a Table L which provides localization information about the set of second DNA sequences relative to the set of first DNA sequences. Next there is the step of operating the processor on Table L to produce a map of the genome which determines where the set of first DNA sequences are located within the genome. Then there is the step of producing a gene in the genome map. Preferably, after the producing step, there is the step of purifying derivatives of the gene produced. Also, the first DNA sequences are preferably STSs, the second DNA sequences are YACs, and the DNA sequence fragments are radiation hybrids.

The present invention pertains to a process for efficiently and accurately constructing indirectly high-resolution maps of genomes and other entities. Specifically, the process comprises the steps of generating three sets of reagents, namely, (1) sample points, (2) covering regions, and (3) probes; performing parallel experiments to efficiently compare these reagents and acquire two data tables, one of (a) probes with covering regions, and another of (b) covering regions with sample points; combining these two independent tables by means of an inner product operation to produce a third table that indirectly compares probes with sample points; analyzing this computed table to construct a high-resolution map of the probes, the sample points, and the covering regions. The resulting integrated map is then used to efficiently search for probes based on their proximity to selected sample points. With genome maps, this search can enable the rapid discovery of genes, their products, and their useful applications.

BRIEF DESCRIPTION OF THE DRAWINGS

In the accompanying drawings, the preferred embodiment of the invention and preferred methods of practicing the invention are illustrated in which:

FIG. 1 is a Table A of YAC vs. RH comparison data.

FIG. 4 is a Table L of the YAC vs. STS comparison matrix computed by IPM using an arithmetic inner product that sums all the matches.

DESCRIPTION OF THE PREFERRED EMBODIMENT

Figure 7:
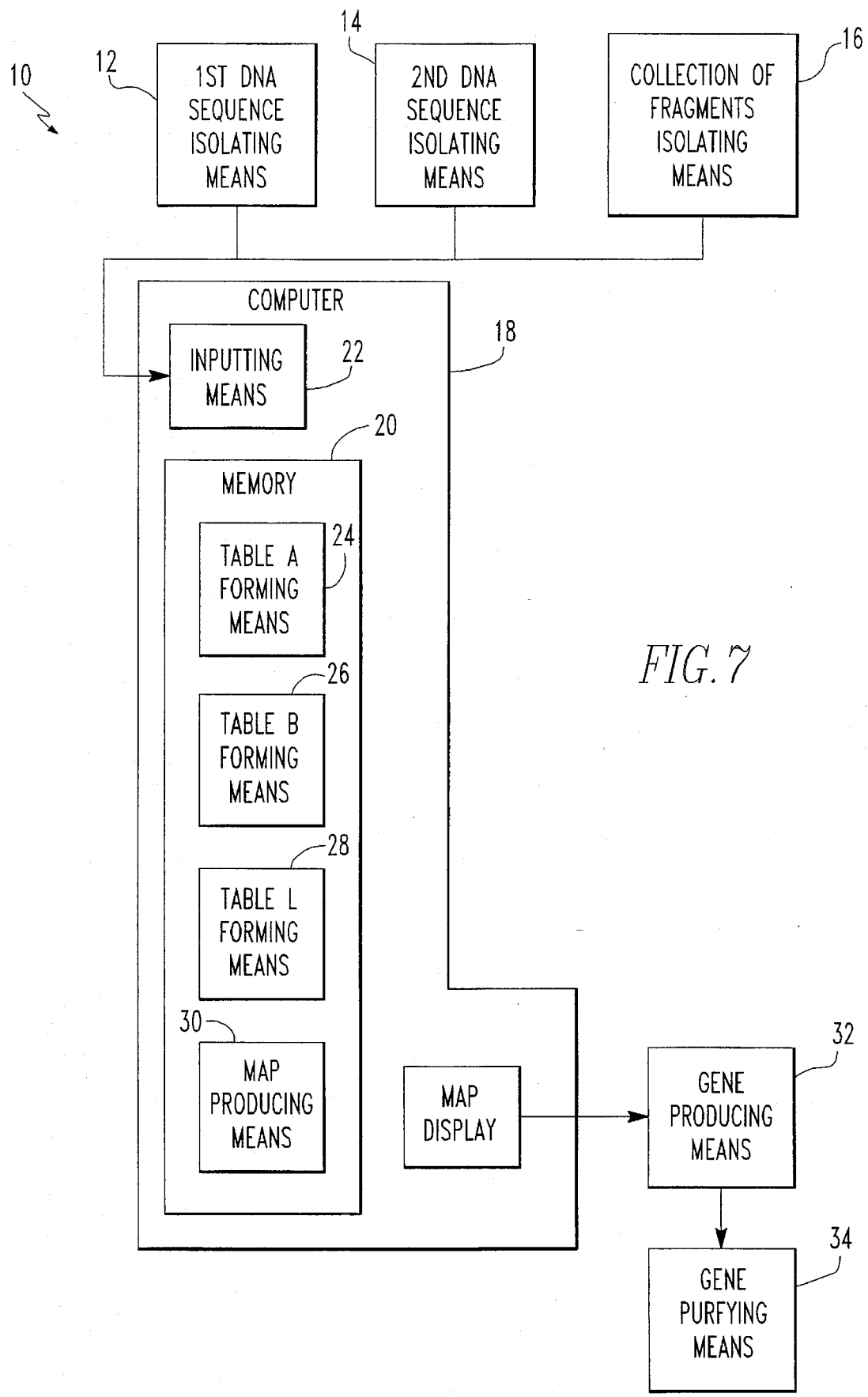
FIG. 7 is a schematic representation of a system of the present invention.

Referring now to the drawings wherein like reference numerals refer to similar or identical parts throughout the several views, and more specifically to FIG. 7 thereof, there is shown a schematic representation of a system 10 for cloning a gene of a genome. The system 10 comprises means 12 for isolating a sufficiently large set of first DNA sequences having a size between 100 b–40 kb to achieve a desired resolution. Each first DNA sequence is part of the genome. For instance, for STSs of well-characterized species (man, mouse, etc.), the first DNA sequence isolating means preferably entails looking up (in journals or databases) the PCR primers (or sequences) of known STSs, and then constructing the primers using a DNA synthesizer. Alternatively, the original laboratories can be contacted to provide DNA sequence primers for the STSs. In species that have not yet been well characterized, genetically useful highly polymorphic STSs can be constructed by building CA (or other tandem nucleotide) repeat markers. These are found by using complementary DNA (e.g., GT polymers) as PCR primers, and expressing and isolating matching CA-repeat sequences from digested DNA fragments. Characterization, leading to eventual sequencing, can identify an entire library of polymorphic markers.

The system 10 also comprises means 14 for isolating a sufficiently large set of second DNA sequences having a size between 40 kb–2 mb to achieve the desired resolution. Each second DNA sequence is part of the genome. For instance, for a cosmid library, the second DNA sequence isolating means entails purchasing the requisite n-hit library from one of many companies which advertise in molecular biology journals; the current cost is about $5,000. For a human YAC library, this entails contacting one of many Human Genome Centers, and requesting the clones or panels.

Alternatively, one could construct such a library by dilution-limited restriction enzyme digestion of a genome (or portion thereof), size selection by gel migration, and cloning of appropriate size inserts.

The system 10 additionally comprises means 16 for isolating a sufficiently large set of collection of DNA sequence fragments wherein each fragment's average size is greater than or equal to the size of said second DNA sequence to achieve the desired resolution. Each collection of DNA sequence fragment is part of the genome. For example, the means for isolating a set of collections of DNA fragments can be to build a set of radiation hybrid clones. Further, with IPM, these need not be chromosome specific. For example, to create human radiation hybrid clones, this is done by lethally irradiating (whole genome or chromosome specific) hamster-human hybrid HPRT+ donor cells, and rescuing the irradiated hybrid cells by cell fusion with HPRT-recipient cells. The surviving cells have (1) a HPRT gene from the donor cells, and (2) possibly, a collection of human chromosome fragments. Subsequent screening with human Alu or Line repeat sequences assure that (2) is the case. Another approach is to pool YACs or other large insert clones from library. Such insert clones are created by the mechanisms described above.

The system 10 is comprised of a computer 18 having a memory 20 and means 22 for inputting information into the computer 18 about the set of second DNA sequences, the set of first DNA sequences and the set of collection of DNA sequence fragments.

The system 10 is also comprised of means 24 for forming a Table A in the memory 20. Table A determines the containment or overlap of the set of second DNA sequences against the set of collections of DNA sequence fragments. The system 10 is comprised of means 26 for forming a Table B in the memory 20. Table B determines the containment or overlap of the set of first DNA sequences against the set of collections of DNA sequence fragments. There is also means 28 for forming a Table L from Table A and Table B. Table L provides localization information about the set of second DNA sequences relative to the set of first DNA sequences. The system 10 is also comprised of means for producing a map of the gene from Table L. The map producing means 30 is disposed in the memory 20. The map determines where the set of first DNA sequences are located within the genome and where the set of second DNA sequences are located within the genome. The means for producing Table A, the means for producing Table B, the means for producing Table L and the means for producing the map can preferably be the technique described below. The system 10 additionally is comprised of means 32 for producing a gene of the genome from the map. Preferably, the system 10 also includes means 34 for purifying derivatives of the gene produced in the gene producing means 32. Additionally, the first set of DNA sequences are preferably STSs, the second set of DNA sequences are YACs and the DNA sequence fragments are radiation hybrids.

Figure 8:
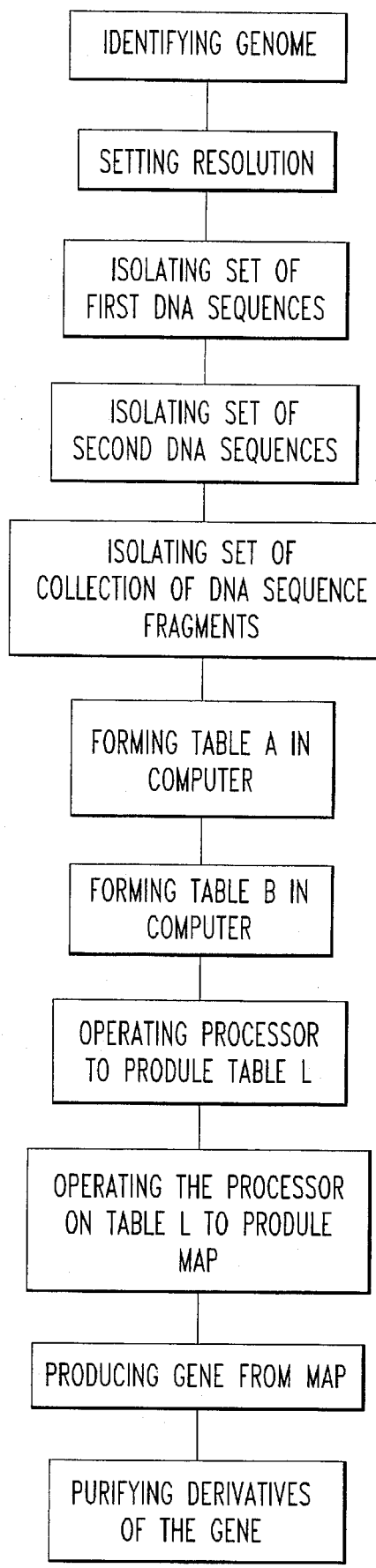
FIG. 8 is a flow chart of a method for cloning a gene of the present invention.
Figure 9:
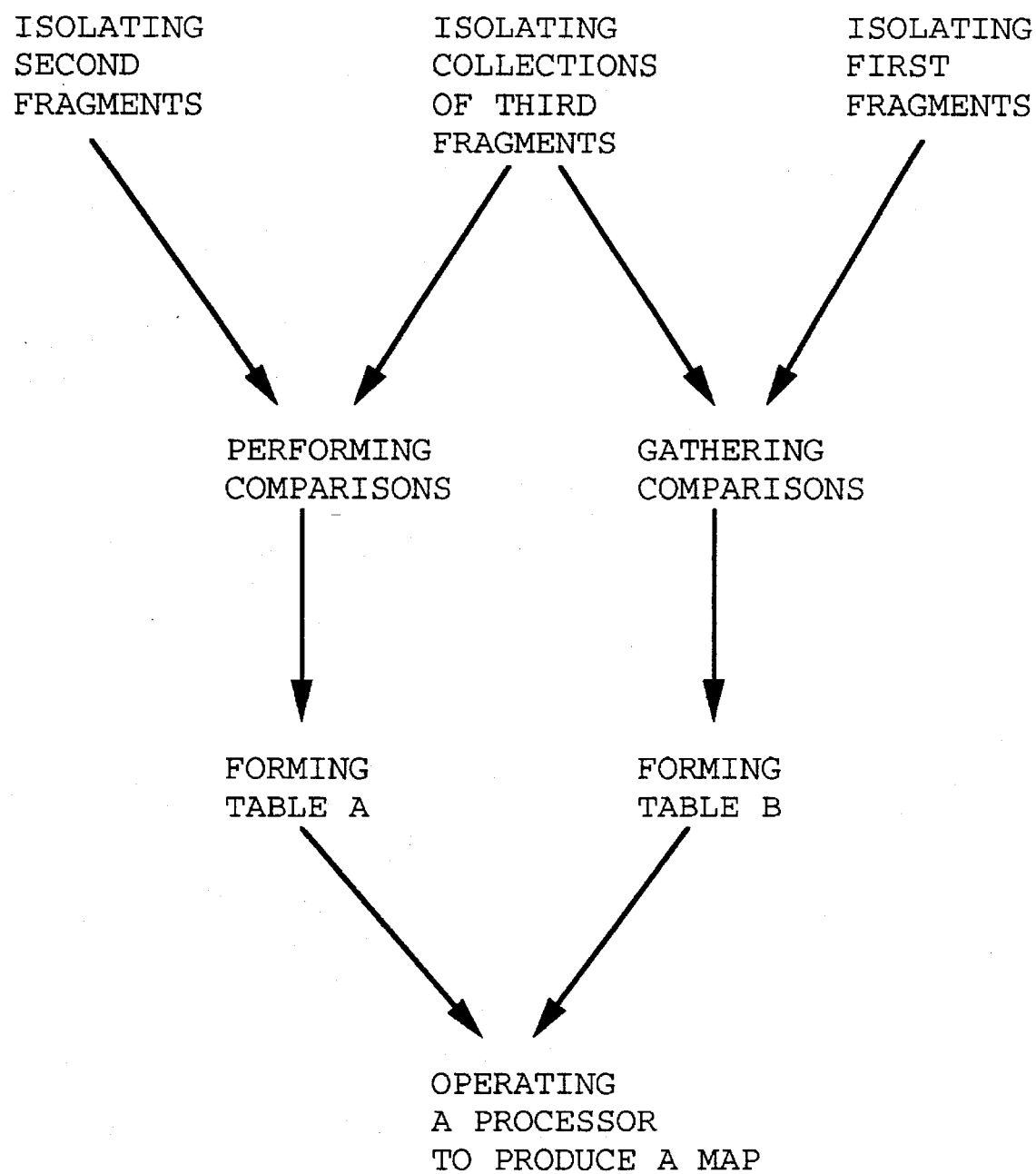
FIG. 9 is a flow chart that shows the combination of DNA resources to form Tables A and B, and then construct a clone map.

The present invention also pertains to a method for producing a gene. The method comprises the steps of isolating a gene from a map constructed by using radiation hybrids. Then there is the step of producing a gene isolated from the map. Preferably, the method of cloning a gene of a genome comprises the steps of identifying a portion of a genome to be mapped, as shown in FIG. 8. Then there is the step of setting a desired resolution of the map. Then there is the step of isolating a sufficiently large set of first DNA sequences having a size between 100 b–40 kb to achieve this desired resolution. Each first DNA sequence is part of the genome. Then there is the step of isolating a sufficiently large set of second DNA sequences having a size between 40 kb–2 mb to achieve the desired resolution. Each second DNA sequence is part of the genome. Next there is the step of isolating a sufficiently large set of collections of DNA sequence fragments wherein each fragment's average size is greater than or equal to the size of each of said second DNA sequences to achieve the desired resolution. Each collection of DNA sequence fragment is part of the genome. Next there is the step of forming a Table A in the memory of a computer 18. Table A determines the containment or overlap of the set of second DNA sequences against the set of collections of DNA sequence fragments. Next there is the step of forming a Table B in the memory 20. Table B determines the containment or overlap of the set of first DNA sequences against the set of collections of DNA sequence fragments. Next there is the step of operating a processor of the computer 18 on Table A and Table B to produce a Table L which provides localization information about the set of second DNA sequences relative to the set of first DNA sequences. Then there is the step of operating the processor on Table L to produce a map of the gene which determines where the set of first DNA sequences are located within the gene and where the set of second DNA sequences are located within the gene. Then there is the step of producing a gene from the map. Preferably, after the producing step, there is the step of purifying derivatives of the gene produced. Moreover, the first DNA sequences are preferably STSs, the second DNA sequences are preferably YACs and the DNA sequence fragments are preferably radiation hybrids.

More specifically, the task is to find the location of every probe (belonging to a set of probes) in some (e.g., spatiotemporal, multivariate) coordinate system. A probe may be thought of as some ball of any small (even zero) to medium size volume in the space. Initially,

- it is known that each probe resides at some fixed location;
- it is not known what this location is;
- the coordinate system is described by a set of sample points;
- it is not necessary to know the location of these coordinate sample points.

Under these conditions, the objective is to build a map of where the probes (and, possibly, the sample points) reside in the coordinate system.

There are two possible strategies to determine the locations of the probes (and, possibly, the sample points). The first is to directly compare each probe against each sample point, and determine whether or not this probe/point pair overlaps, recording the ± response. When there is no guarantee that each probe overlaps at least one sample point (e.g., too few sample points, or very small volume probes), this direct method cannot work.

The second, novel, strategy presented here is to perform indirect comparison experiments via an intermediate set of independent covering regions, and then computationally combine these comparison results to build a map of the probes (and, when necessary, the sample points). A set of covering regions is selected, which are neither probes or sample points. One covering region is comprised of a set of separate, individually connected and fairly large, subregions. The total volume of all these subregions (for one covering region) covers a large volume (say, half) of the coordinate space.

- Each probe is compared against each covering region entity for overlap, constructing a data table A.
- Each covering region is compared against each sample point for overlap, constructing a data table B.
- Tables A and B are then multiplied as matrices under a suitable generalized inner product operation that performs a matching operation.
- The result is Table L, which indirectly compares each probe with each sample point, thereby localizing the probe in the coordinate space.
- If the locations of the sample points are not initially known, and there is a sufficient number of comparison experiments, the method can additionally determine the position of each sample point in the coordinate space. I.e., it can map out the coordinate space via its sample points.

This indirect mapping technique is called Inner Product Mapping, or IPM. It works as follows.

Suppose that the location of the sample points are entirely known (eventually this assumption will be relaxed). To fix ideas, suppose that the coordinate space is finite, two-dimensional, and covered by a uniform grid of sample points. Further suppose that the probes are too small relative to the sample points to be reliably detected. I.e., direct mapping cannot work here, and the indirect IPM method is required.

To use IPM, a suitable set of covering regions are first identified. They are selected to be properties of the coordinate space that roughly cover 50% of the area. For concreteness, suppose that the two-dimensional coordinate space is actually some small geographical area. And, that the probes can perform measurements in this area to ascertain whether or not they reside in a covering region. In this example, likely covering regions might be:

Elevation—Is the altitude above 100 feet?

Vegetation—Does some (fairly ubiquitous) plant grow here?

Pollution—Is the region polluted by some chemical?

Further suppose that the probes are too small relative to the entirely independent of one another.

Now, one tries to locate a given probe.

(1) The probe tests the elevation, and returns a "+"; it is indeed over 100 feet. This partial localization reduces the search area to ½ of the total space.

(2A) The probe then tests the vegetation, and records a "−": the plant does not grow at the probe's location. This is another partial localization, to the complement of the vegetation covering region, that reduces the possible area by ½.

(2B) By combining the independent results of (1) and (2), and intersecting the elevation covering region, together with the complement of the vegetation covering region, the probe is localized to ¼ (=½×½) the total area.

(3) Continuing in this way, the probe would then test the third covering region. Suppose the result was "+", indicating pollution. Intersecting this covering region with the previous results would localize the probe ⅛ (=½×½×½) the area.

Thus, the ± signature vector of the probe against each of the covering regions provides a mechanism for rapid, precise locationalization. By intersecting regions or their complements, according to the "+" or "−" result, IPM effects localization. And, since each new region incrementally reduces the possible probe area by (roughly) ½, the IPM method has exponential power in the number of covering regions.

Mathematically, this result can be described as the inner product of the probe's signature vector a against a matrix B of covering regions. Each row of B characterizes one covering region in terms of the space's sample points. Multiplication of a "+" vector component with a row selects the (sampled) covering region, while multiplication by "−" selects the complement of the covering region. This can be thought of as an equivalence operation: + with +, or − with −, yields +; + with −, or − with +, yields −.

The inner product combines these component multiplication results by intersecting them. With conjunctive intersection, for example, a sample point is inferred to be close to a probe only when its covering region signature is identical to (i.e., equivalent for every covering region) the probe's covering region signature. There are other, less restrictive, ways of combining the partial results. For example, those points which have the greatest number of equivalences could be inferred as closest to the probe.

The common property to all such inner product definitions is the notion of signature match. Every probe and sample point has its own signature, determined by independent experiments against the covering regions. In essence, the inner product operation looks for the closest match between the probe's signature vector and one (or more) sample point's signature(s). The point(s) having the best matching signature is inferred to be in closest proximity to the probe. In practice, a local neighborhood, rather than just one point, may be matched.

Notationally, it is written as:

$$l = a \times B,$$

where l is the probe's localization vector containing the Boolean or numerical localization values. The peak of this curve localizes the probe with respect to the sample points. The shape of the (numerical match) curve is Gaussian-like.

a is the probe's signature vector (i.e., covering region comparisons).

x is the particular inner product operation.

B is the matrix of covering region vs. sample point comparisons.

Each row of B describes one covering region in terms of sample points. Conversely, each column of B provides one sample point's comparison signature against the covering regions.

It is often the case that multiple probes must be localized. If each probe can perform its tests on the covering regions independently of the other probes, then much experiment parallelization can be achieved. (The same holds true experimently for testing multiple sample points against the covering regions.) Instead of just one probe's signature row vector a, a signature matrix A is written, each row of which provides the signature of a distinct probe.

Mathematically, then, a matrix a of probe signature row vectors is obtained. Performing all the probe localization computations in one process, it is therefore written:

$$L = A \times B,$$

where each row of matrix L localizes one probe.

The key mathematical fact is that

THEOREM: Each row of L localizes its probe in the space.

That is, by obtaining probe vs. covering space comparisons (Table A), and covering space vs. sample point comparisons (Table B), the inner product of A and B does indeed compute an effective comparison of the probes vs. the sample points, i.e., the location of the probe.

The theorem has several useful corollaries, such as:

Corollary. When the probes are uniformly distributed, and each probe resides at a single location, then, up to row permutation, L resembles a (broadened) identity matrix.

Suppose that the positions of neither the probes nor the sample points are initially known. Further suppose that the covering regions are not explicitly known, and are, in fact, only measurable by performing comparisons against probes or points. That is, much data can be generated, but there is absolutely no localization information about probes, covering regions, or sample points.

A key feature of IPM is that from such comparison experiments, full localization information can be accurately inferred.

For clarity, consider the one dimensional case (e.g., chromosome mapping) where the space is a finite line segment (e.g., a chromosome). When the proper column permutation p is known, the (suitably modified) IPM localization theorem $$L = A \times B \times p$$

will hold. In that case, every row of L will have the shape of a stretched Gaussian-like curve. However, with the wrong column permutation p'≠p, the product L=A×B×p' will scatter the row peaks all over the rows.

It is straightforward to construct a heuristic h(row) that is minimized precisely when the row assumes a Gaussian-like, single-peaked, shape. Elements of this heuristic that may cluster maxima include:

minimizing the curve's line length;

forcing the maxima to lie close to one other;

maximizing separation between putative peaks and surrounding regions.

If a good predicted curve shape is available, an L2 norm can be used (i.e., a function space inner product) to minimize the functional distance between the observed and predicted functions. Specifically, the predicted template function is placed at every spatial coordinate, and the L2 difference between it and the data is computed; the smallest such L2 difference is h(row).

Regardless, a function can be readily specified that determines the deviation of a row from the desired peaked shape. A global matrix error function g(matrix) is then computed by summing h(row) over all the rows.

Using (1) the IPM Theorem, together with (2) such a matrix error function, a global search technique that minimizes the total deviation (such as simulated annealing) can rapidly and accurately converge to a correct permutation p. (There may be more than one permutation that satisfy the data.) In the one dimensional case, this amounts to properly ordering the sample points. The power of this method increases with the number of probes: the greater the quantity of unlocalized data, the greater the localization capability.

By modeling or simulation, the precise shape of the row function can be determined. This is used to compute the precise spatial location of the sample points (i.e., not just their relative ordering). This is done by specifying a functional that computes the deviation of each probe's observed row function from its predicted shape. The spatial location of each sample point is slightly adjusted to minimize the overall deviation (for all the probes), say by local relaxation methods. Thus, the underlying space is locally stretched into its proper shape, thereby determining the spatial location of every sample point.

In summary, then, one starts with a large of set of probes, and a large set of sample points, both with unknown locations in some space. An (also unlocalized) set of intermediate covering regions are selected. Comparison experiments of the probes vs. the regions are performed, to obtain table A, and of the regions vs. the points to obtain table B. Inner product mapping then computationally combines tables A and B to accurately determine:

the location of every probe (in terms of the sample points), the location of every sample point (as a coordinate in the space), and the spatial extent of every covering region.

One concrete application of IPM is in efficiently constructing integrated genetic/physical maps of chromosomes (or entire genomes). That is, the space here is a one dimensional line of finite length. Suppose one has a dense (e.g., 1 megabase (MB) resolution) set of sample points along the chromosome comprised of genetic/physical markers, such as the PCR-based sequence-tagged sites (STSs). Further suppose that one also had physical probes of DNA sequences, such as yeast artificial chromosomes (YACs) or cosmids. Now, assume that both the sample points and the probes were accurately mapped along the one dimensional chromosome. Then, useful genes could be rapidly found by positional cloning:

Perform genetic family studies of a disease to localize the causative gene(s) along the genetic point map.

Look up the gene point's position in map coordinates.

Retrieve the corresponding physical probes at that map location.

Determine the DNA sequences of the probes.

Identify the few candidate genes on the probes.

Select (and verify) the causative gene.

With the causative gene(s), one can (1) immediately devise diagnostic tests based on DNA markers, (2) better understand the disease by translating the DNA into its protein product and performing further experimentation, and (3) ultimately develop a cure, based on either the gene's DNA, its protein product, or resulting improved understanding of the disease mechanism.

To map a genome using IPM, then, one needs three reagents:

Points.

These can be STSs, or fluorescence-based in situ hybridization (FISH) studies. Any measurement that can sample the chromosome space will suffice.

Lines.

These DNA probes can be large, such as YACs, or smaller sized, such as cosmids or plasmids.

Covering Regions.

Radiation hybrids (RHs) are ideally suited to the task. Each RH is a set of large (randomly generated) chromosomal subregions that is preserved in a hamster cell culture clone. Other candidate reagents, such as pooled YACs, are discussed below.

Two sets of experiments are performed to obtain two data tables. These can be done on a single chromosome, or on an entire genome.

Table A.

The line probes (rows) are compared against the covering regions (columns). The extent of reaction, on a graded scale of −1 to +1 is recorded for each comparison. For parallelization, this can be done by obtaining each row or column in one experiment. For example, to obtain one column at a time, one can compare all the rows (probes) with one column (radiation hybrid) at once. This is done by first gridding out the (YAC or cosmid) probe library's DNA onto filters, and then hybridizing with one RH's labelled DNA obtained by inter-ALU PCR.

Table B.

The covering regions (rows) are compared against the sample points (columns). The extent of reaction, on a graded scale of −1 to +1 is recorded for each comparison. For parallelization, this can be done by obtaining each row or column in one experiment. For example, to obtain one column at a time, one can compare all the rows (covering regions) with one column (STS) at once. This is done by first gridding out the RH library's DNA onto filters, and then conducting a PCR experiment for one STS.

Suppose that radiation mapping was first performed on the STSs, and the point locations are therefore known. To determine the probe positions, the matrices A and B would be multiplied under a suitable inner product (say, the standard additive sum over multiplicative product operation) and obtain the product matrix L. In each row of L, the location of the probe would be suggested by a (Gaussian-like) unimodal curve. Taking the average of the maxima of the curve would give an estimate of the peak's spatial position, i.e., the probe's chromosome location. A more sophisticated approach would fit the observed curve neighborhood to a predicted curve shape, and use the fitting parameters to compute the peak location.

Suppose now that RH mapping were not done first, and that there was absolutely no localization information about the sample points. The inner product of data Tables A and B would still be used to compute L. However, since the columns of L (i.e., the STS point ordering) would be (almost certainly) incorrectly permuted, L would not provide the localization. Rather, an error function would be computed from L (as described above) that estimated the deviation from the expected unimodal curves in every row of L. Coupled with a global search procedure (such as simulated annealing), alternative permutations would be explored to minimize the error function. When minimized, an approximately correct column permutation would be found, and both L and the STS ordering would be found. The distances between the STSs would be computed by local relaxation techniques (outlined above) that minimized an error function of predicted vs. observed curve shapes, over all the probes. Then, with the point locations known, one would proceed as in the preceding paragraph to determine the probe locations.

The spatial resolution is set by the number of "bins" constructed by the intersections of covering regions. To fix ideas, consider the one dimensional case of radiation hybrids. Suppose that a RH, on average, contains five fragments and five gaps; this generates ten bins per RH. Combining k RHs will then generate, approximately, 10*k bins. Each such multi-RH bin will have a relatively unique signature vector of k "±" values, out the 2^k possible signature vectors. An increased number of fragments and gaps per RH will lead to more bins, hence greater resolution, per RH.

The sample points, e.g., the STSs used in chromosome mapping, serve to populate the bins with measurable reagents. The number of points sets the final resolution of the system. As described above, as additional RHs are incrementally deployed, the resolution of the system improves exponentially. Once every point is in its own unique bin, the maximum resolution is attained. Beyond this, additional RHs serve primarily to overcome noise in the system.

How does localization vary with probe volume? With genome mapping, probe volume corresponds to the length of the DNA insert of the YAC, cosmid, or other vector. The best resolution is achieved with point size probes, i.e., at zero volume. Larger probes act to locally smooth over a wider neighborhood of spatial bins. This might appear to worsen resolution as probe size increased. In fact, however, by fitting the expected broadened curve to the observed data, the true probe center can be localized with little or no loss of resolution.

This example of IPM for chromosome mapping assumes that the order (and distances) of the STS probes are known. If they are not known, then, as detailed above, one can use the IPM product, together with a global search mechanism, to search for the correct ordering. (Specifically, with the correct ordering, the product matrix must have each matrix row take the form of a broad, single peak function. A global search such as simulated annealing can permute the matrix product columns to find the best STS ordering. Subsequent curve fitting with local relaxation methods will then determine inter-point distances.)

This specific example was constructed using our IPM simulation, visualization, and analysis software. Suppose that the chromosome length is 100 megabases (MB). Fifty random STSs are used, which sets an average inter-STS distance of 2.0 MB, i.e., the resolution of the map. Thirty-two radiation hybrids are used, with a fragment retention probability of 0.30, and an average inter-break distance of 5.0 MB; this provides sufficient bins for our 50 sample points. Twenty-five YAC insert probes are examined, with an average insert size of 0.100 MB, uniformly distributed over a range of ±0.020 MB.

Figure 1:
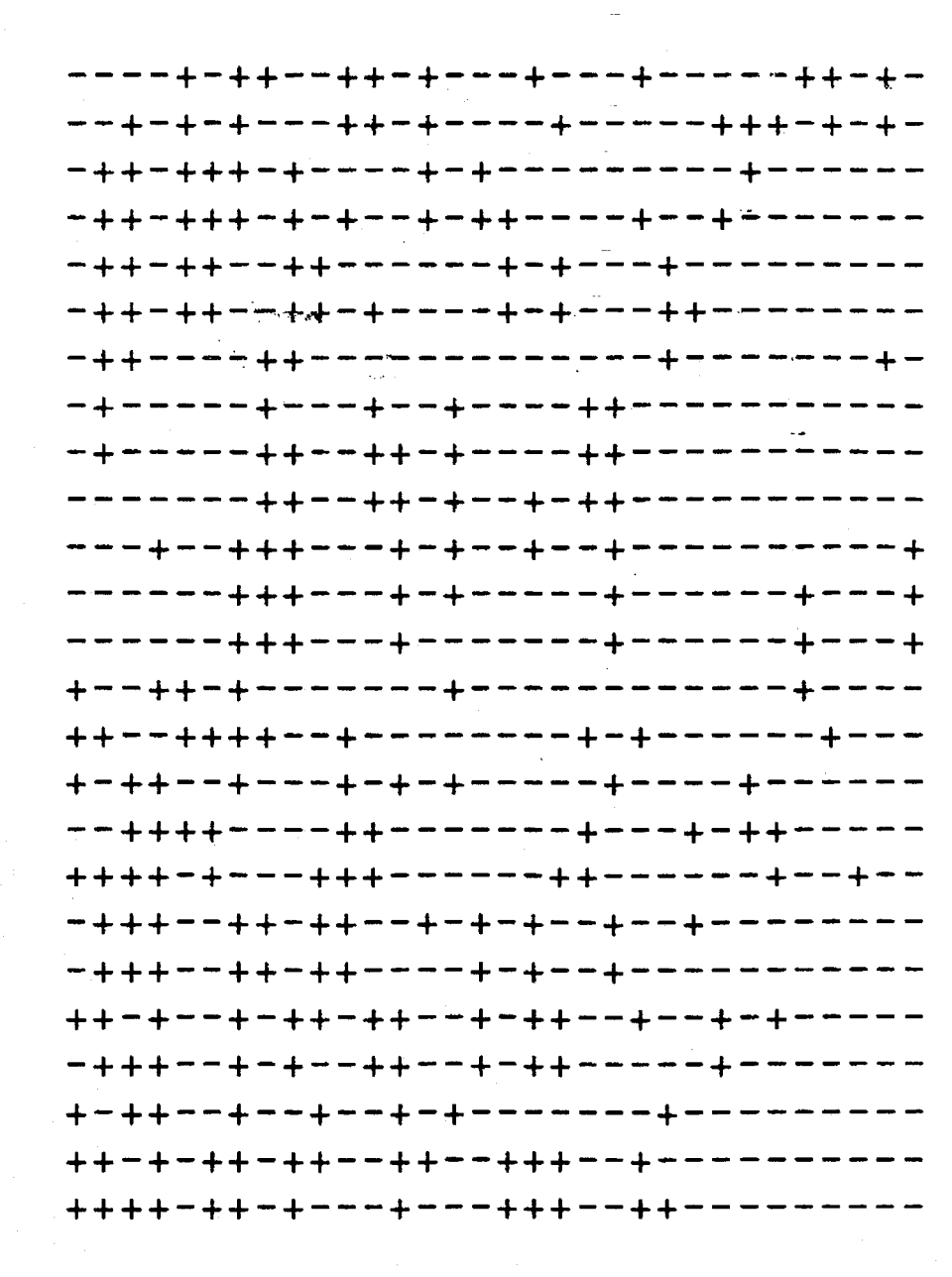

To construct Table A, the YAC probes are compared for overlap against the RH covering regions. This may be done in parallel one column at a time by first preparing gridded filters, each of which contains a dense array of YAC DNA. This DNA is obtained, for example, by amplification with interspersed repetitive sequence (IRS) (e.g., Alu or L-1) PCR. Then, each RH's DNA is similarly amplified by IRS-PCR, and the labelled product is hybridized against the YAC filters. The hybridizations are scored as ± comparisons, and recorded. The result is the Table A of YACs vs. RHs, shown in FIG. 1. Each row of the table provides a YAC with a unique RH signature vector.

Figure 2:
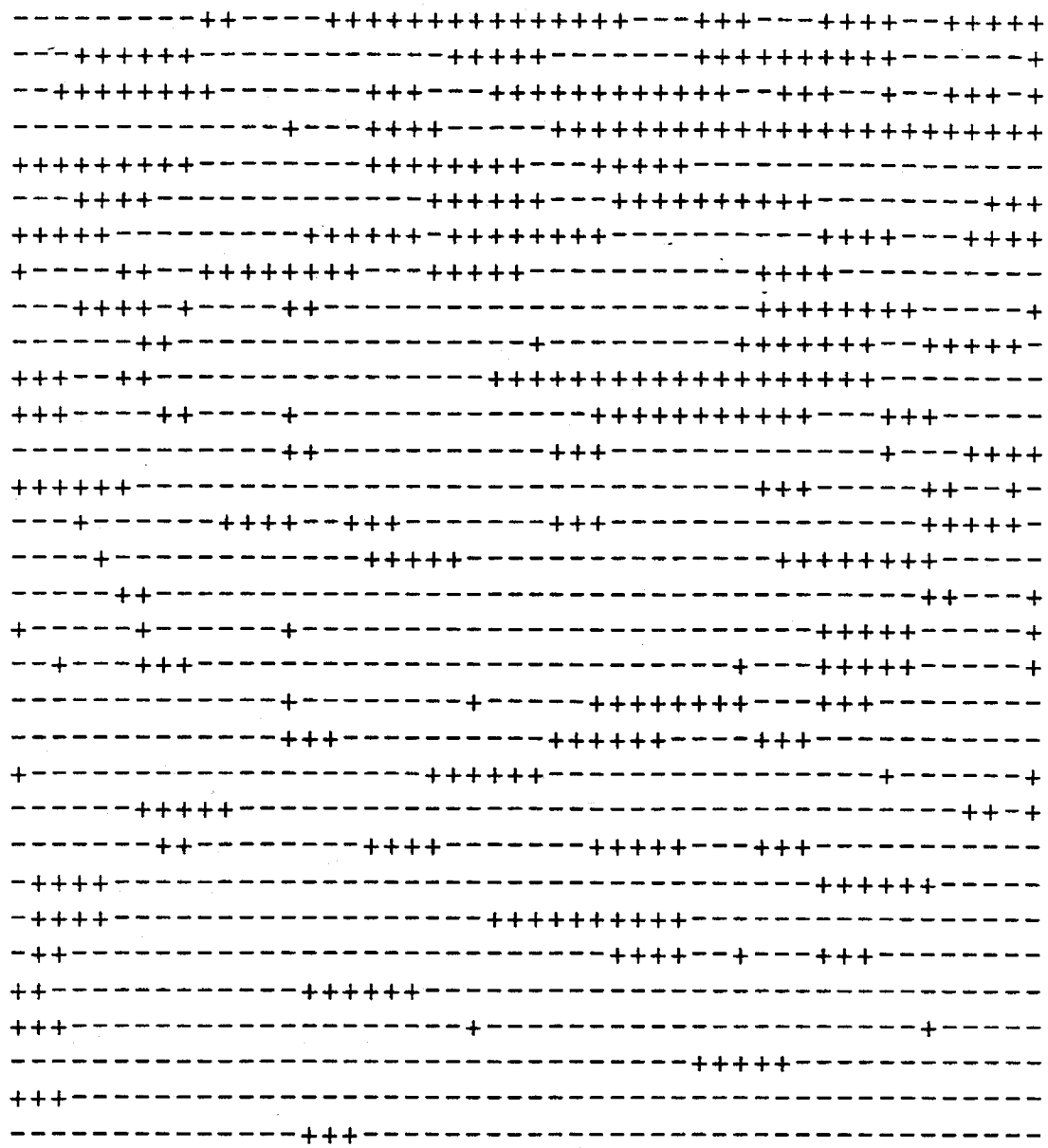
FIG. 2 is a Table B of RH vs. STS comparison data.

To construct Table B, every RH is compared against every sample point to determine whether or not the point is contained in (or overlaps with) some RH fragment. This can be done in parallel either one row or one column at a time. For example, one can test each point against all the RHs at once. With STS sample points, this is done by first preparing gridded filters of RH DNA products; each filter contains the extracted and amplified DNA of all the RH clones, each RH located at its unique coordinate. PCR is then performed using labelled primers with one STS against all the RHs on the filter. The ± comparisons are then scored and recorded. The resulting Table B of the RHs vs. the STS is shown in FIG. 2. Each column of Table B provides an RH signature vector for some STS sample point.

Figure 3:
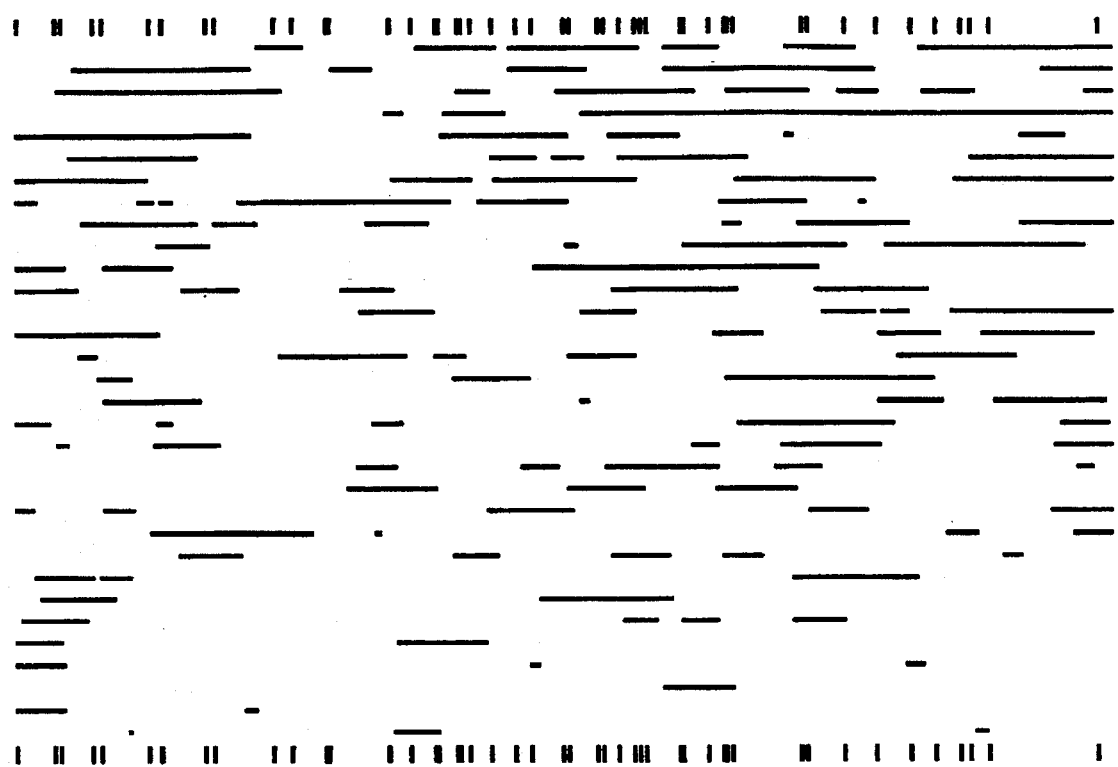
FIG. 3 is an RH fragment/gap pattern. Each row represents one RH. The tick marks above and below the diagram shows the true locations of the STS sample points.

Note how each row of the table provides a sampling of one RH's fragment/gap pattern (contiguous +'s or −'s) along the chromosome. Compare this with the true RH locations shown in FIG. 3 below.

Figure 4:
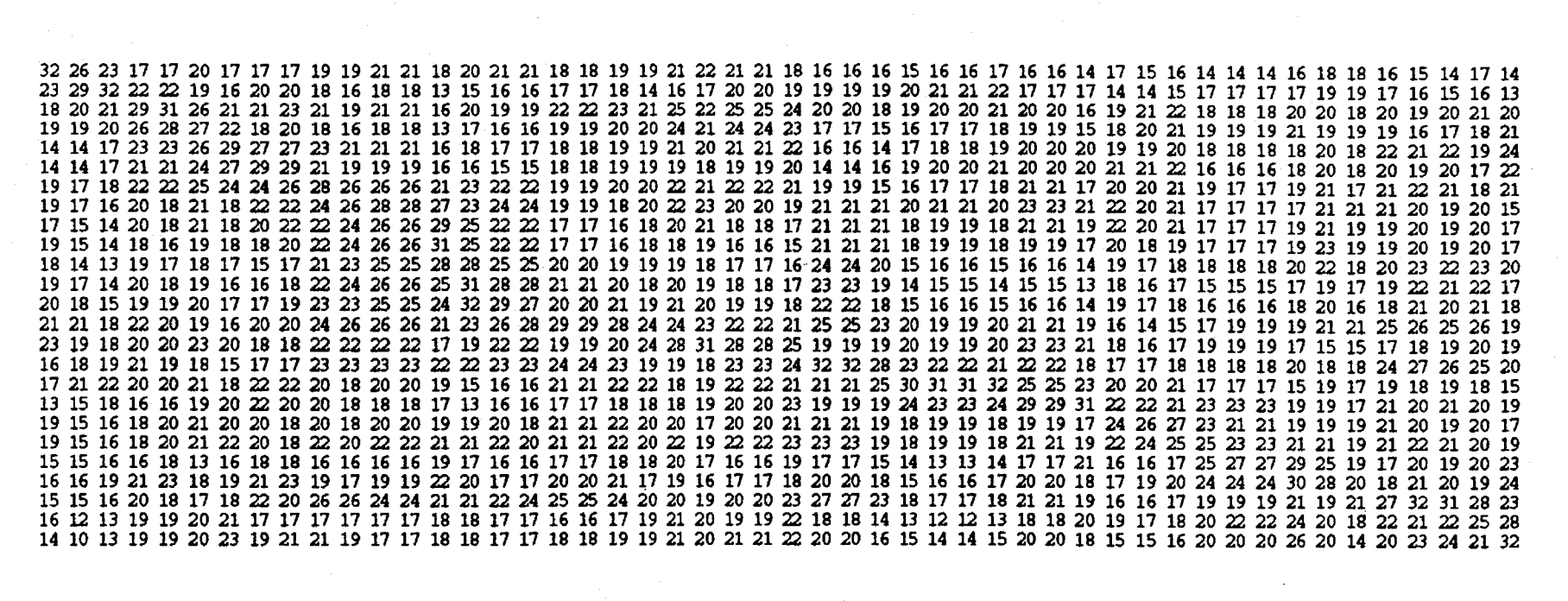

The Tables A and B are treated as matrices, and multiplied together under a suitable inner product. Here, we use the sum over the product. The result, shown in FIG. 4, is a matrix of nonnegative integers, comparing YAC rows against the STS columns.

Figure 5:
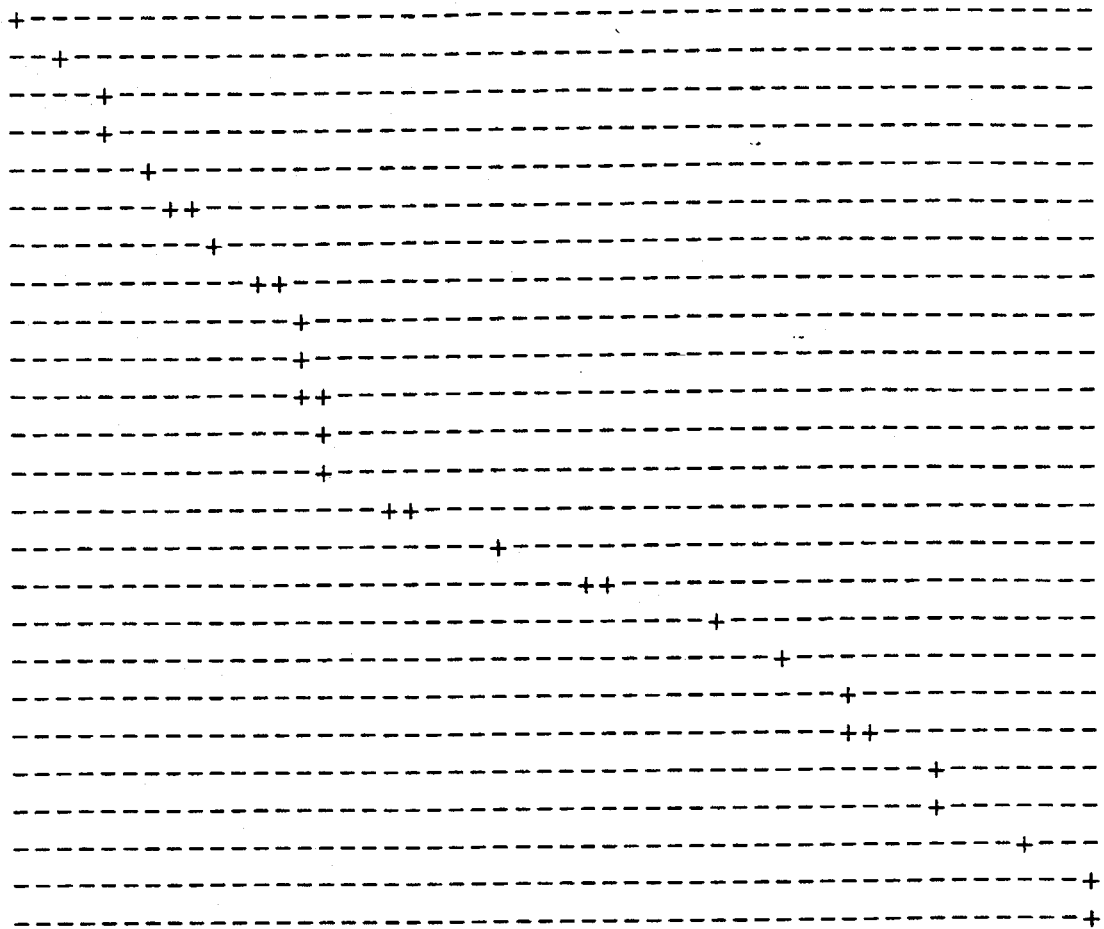
FIG. 5 is a Table A×B of the result of the inner product multiplication of Tables A and B, after thresholding Table L row by row. Both the YAC rows and the STS columns are ordered for better visualization.

Each row is scanned for its peak. For example, with the low noise of this example, it suffices to locate the maxima of each row. This is recorded as a +, and presented in matrix form, as shown in the table of FIG. 5. In each row, the +'s indicate local matches of the YAC's signature against the STS column signatures. Note that the comparison of ordered YACs against ordered STSs shown does indeed result in an approximate identity matrix, visually suggesting the success of the IPM method.

Figure 6:
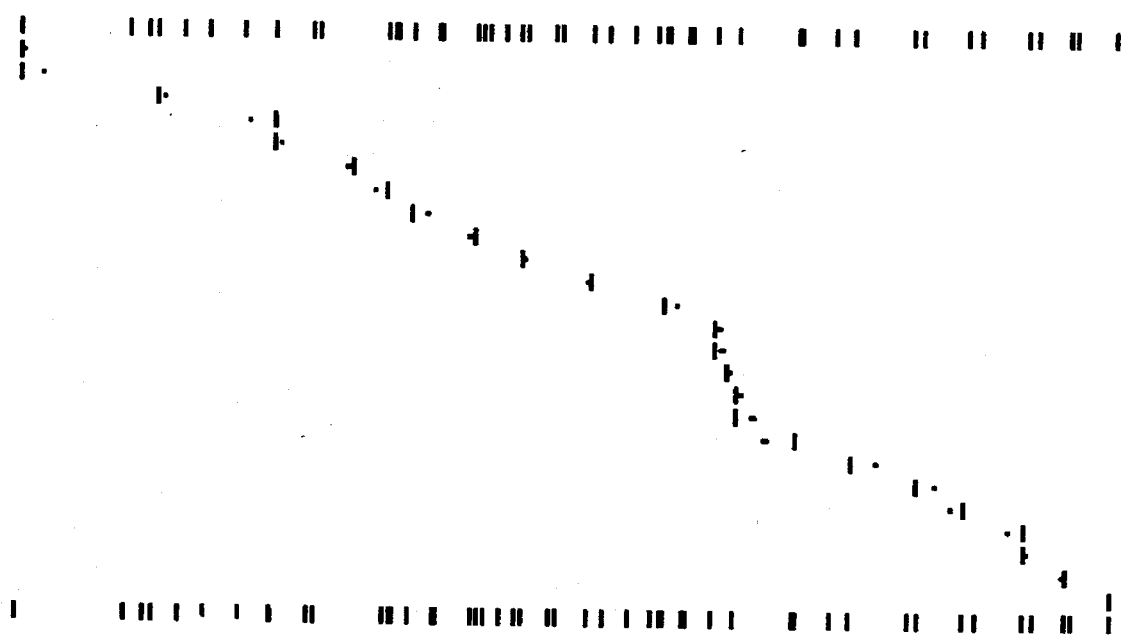
FIG. 6 is a for every row, the predicted YAC center (the row's vertical tick mark) is shown overlain upon the true YAC location (the row's horizontal line).

For more precise localization, these STS positions can be averaged together into a estimate of the YAC's center location. This is shown in FIG. 6, which draws (1) the true STS locations as vertical tick marks at the top and bottom, (2) the true YAC locations as a horizontal line in each row, and (3) the predicted YAC center position as a vertical tick mark shown on the YAC's row. As shown in every row, the predicted center positions (i.e., item 3) lie near or on the true YAC locations (i.e., item 2).

How good is the result? Analysis of the simulation shows that, in reality, only one YAC was even hit by an STS. I.e., direct comparison methods such as STS-content mapping would have completely failed. However, IPM's match-based indirect comparison approach that combines two independent data tables worked quite well. Specifically, the distance between the predicted and true YAC centers ranged from 0.03 MB to 2.80 MB, with an average distance of 0.93MB. This is the best that one can expect from a 2.0 MB inter-STS sampling distance.

The key components of a useful software system for IPM are:

A simulation module that can generate test examples according to different experimental reagents and conditions.

A mapping module that can solve problems using IPM and construct maps.

An analysis module that can assess the utility of the solutions.

A visualization module that can present results and analyses in a visually perspicuous way.

These have been developed and implemented. The current version runs in Common LISP on the Macintosh computer.

Several refinements and extensions to the basic IPM method are now described. These increase the utility, applicability, and power of IPM.

IPM is based on intersections of regions. Positive and negative comparisons of probes against covering regions are equally informative. Therefore, a covering region is most informative when the volume of its covering subregions is about 50% of the total volume. In this case, the volume of the complement of the covering subregions is also about 50%.

The more informative the covering regions, the fewer covering regions required. For example, with only 30% coverage per covering region, the minimal multiplicative reduction by a region or its complement is MAX{p,q}, where p=0.30, and q=0.70. Here, that figure is 0.70. Thus, two covering regions, having a combined localization power of 0.49 (=0.70×0.70) would be needed to achieve about the same localization power of a single 50% covering region. Fortunately, the localization is still exponential: only twice as many (i.e., a constant factor) covering regions are needed.

This combination of covering regions suggests one mechanism for reducing experiments: pool covering regions into fewer (combined) covering regions. With genome mapping, this can be done by pooling the DNA of RHs to effect 50% coverage.

Another pooling strategy enables the elimination of the third set of reagents (i.e., RHs) entirely. Rather than pool covering regions, one can just pool the probes, thereby creating synthetic covering regions with optimal properties. In the case of genome mapping, this would allow the RHs to be entirely dispensed with. Instead, the DNA insert probes (e.g., YACs, cosmids, plasmids, BACs, etc.) would be pooled to form synthetic RHs that cover 50% of the genome or chromosome. This has several advantages:

(1) The need for a third reagent is eliminated. That is, only DNA insert probes and STSs are needed.

(2) The number of experiments can be reduced by using ideal (i.e., 50% coverage) covering regions.

(3) The resolution of each covering region is increased, since the number of bins (fragments or gaps) is increased with synthetic covering regions.

By simulation, mathematical, statistical, neural network, or any other modelling technique, the expected shape of the localization distribution that appears in each row of the product matrix can be determined. This has considerable utility:

(1) The probe center position can be estimated by fitting the observed data to the expected distribution, and then recording the spatial coordinates at the distribution's peak.

(2) The probe size can be estimated by similarly fitting the data to a family of expected distributions that are indexed by probe size. The best fit estimates the probe size.

(3) Suppose that the sample point locations are unknown. Then, a global search mechanism (e.g., simulated annealing) can use a minimization function over the probe vs. point IPM product to determine the point locations. The a priori expected distribution function of the probes can be used (e.g., as an L2 minimization heuristic) to better fit the point locations to the observed data.

(4) In the case of one dimensional spaces such as genomes or chromosomes, item 3 implies both the ordering of STSs, as well as determining the inter STS distances.

Both false negative and false positives are possible, in both Table A and Table B. Using more RHs will provide more unique signature vectors for the probes and points, and thus overcome much of the experimental noise. When coupled with curve fitting, the background noise is essentially eliminated.

Another approach, discussed next, is to modify the inner product operation.

A variety of inner products may be used with IPM. The Boolean inner product (and over equivalence) only works with perfect data. Numerical inner products such as sum over product, where ± comparisons are encoded as +1/−1, allow for more informative post-processing of the rows in the product matrix.

When additional information is available, the inner products can be adapted to use it. For example, with some noisy experiments, the average false negative and false positive rates can be determined experimentally. Then combinations of various observable results can be predicted, and written down as constants. Specifically, a=Prob{true+in A}×Prob{true+in B} b=Prob{true−in A}×Prob{true−in B} c=Prob{true+in A}×Prob{true−in B} d=Prob{true−in A}×Prob{true+in B}

The standard numerical inner product can be rewritten as the equivalent sum of four terms:

$$SUM(+,+)+SUM(-,-)-SUM(+,-)-SUM(-,+),$$

where the (r,s) indicates one of the four possible pairwise comparisons between a ± value r in matrix A and a ± value s in matrix B. Accounting for combinations of false negative and false positive rates in tables A and B amounts to weighting this inner product by the constants a, b, c, and d:

$$aSUM(+,+)+bSUM(-,-)-cSUM(+,-)-dSUM(-,+)$$

The resulting sum is then a better predictor of true match.

Another inner product operation can be constructed to account for the a priori coverage at the covering regions. Specifically, a probability or likelihood can be computed from the Table A or Table B data that adjusts each component inner product multiplicand by the odds at the observed result. For example, if p is the fraction of +'s for the Kth covering region and ++ match is observed, then the Kth multiplicand in the inner product could be adjusted by a factor such as 1/p.

The experimental results are not always discrete all-or-none comparisons. Uncertainty and intermediate results are observed. Therefore, inner products that accommodate continuous values (say, between −1 and +1) are useful. One such inner product is the sum of the products. This can be further adapted, say for false negative or false positive distributions, as shown above.

When the sample point locations are unknown, a global search mechanism (e.g., simulated annealing) can use a minimization function over the probe vs. point IPM product to determine the point locations. The key idea is that, in each row, the shape of the product forms a broad Gaussian-like peak, and not a delta function. This broadening in the probe vs. point product can be exploited to determine sample point positions.

When all the points are correctly localized, then the IPM product will localize every probe to its proper location. That is, every probe will be characterized by a broad Gaussian-like distribution, with the center of the distribution located at the true center of the probe. I.e., the probe occupies some localized density in the space.

When the point locations are not correctly localized, then, for each probe, this density will be scattered across the space. An error function (between observed and predicted) can compute the extent of this scattering. The error function can be heuristic (looking merely for densities), and/or highly specific (e.g., the L2 deviation from a probe's predicted distribution function).

A global search mechanism (such as simulated annealing) can shuffle the sample points around the space. When the points move toward their correct position, the probe densities are less scattered, and the error function is minimized. Iterating this process to minimize the error will unscatter an entire set of probe densities, and thus correctly localize (within some error) all the sample points.

Importantly, the more probes tested, the better the error function. That is, as the amount of data increases, little extra computational effort is required, but the algorithm better converges to the true locations.

The current best method for Radiation Hybrid mapping is break minimization and its derivatives. The equivalent of Table B (RHs vs. STSs) is experimentally constructed, and then the STS columns are permuted to minimize the number of obligate breaks. That is, a global search (e.g., using simulated annealing) is done, where the error function is the number of transitions between + and − in Table B.

IPM provides a more principled mechanism that can reduce the number of required experiments. Specifically, obtain Table B. Then set Table A equal to the transpose of Table B. When the correct STS ordering (and distances) are obtained, each row of the product matrix should resemble a unimodal Gaussian-like function. Thus, using the method of previous subsection (on determining sample point position), RH mapping can be effected.

Advantages include:

(1) IPM knows the shape of the predicted row product distributions, where as the break minimization method has no such distribution information available to it. This can improve the accuracy of the STS ordering and inter-STS distances.

(2) The use of IPM may (exponentially) reduce the number of required RHs and RH experiments, thereby reducing expense.

Or, it can be for constructing ordered probe maps, wherein only Table A (the comparison of DNA sequence probes against radiation hybrids) is obtained. Table B is then set equal to the transpose of Table A. The product matrix L is then a symmetric matrix which compares each probe with every other probe. Each entry in L is the inner product of the radiation hybrid signatures of two probes. The resulting map then localizes the probes, without the need for STS reagents nor with comparisons of the radiation hybrids against STSs.

The objective for three-dimensional visualization of chromosomes is to effectively visualize many genomic probes against the entire genome in a single fluorescent microscopy experiment. The technology for visualizing DNA probes on chromosomes is still in its infancy. The current best techniques use two dimensional (2D) light microscopy to measure multiple fluorescent DNA probes at precise locations along a chromosome. One key limitation is the resource intensive search for (rare) neatly arrayed metaphase chromosomes. Restricting precision is the microscope's 2D projection of three dimensional (3D) chromosomes. Further, assigning one fluor to one chromosome (for twenty three chromosomes) is beyond the resolving capabilities of fluorescence detection. These problems can be solved by using 3D microscopy and multiplexed pooling of fluorescent DNA probes, coupled with Inner Product Mapping (IPM), to visualize (common) interphase nuclei.

One chromosome can be readily visualized using a single fluor attached to multiple DNA markers along its length. Ideally, then, all 23 human chromosomes could be visualized by using 23 distinct flours. With IPM's pooled multiplexing arrangement, though, only five (i.e., log2(23)) are needed; further, this smaller number (i.e., 5) is experimentally feasible. The idea is to use each fluor to label multiple chromosomes in a single interphase nucleus, obtain five separate images, and then use IPM to combine images and their intersections to mathematically visualize each individual chromosome.

The result is a 3D map of the interphase chromosomes. Using additional fluors, labeled DNA probes can then be precisely mapped to chromosomal locations. For example, inter-Alu PCR of genomic RHs can be used to localize the RH fragments on the chromosomes. Similarly, DNA disease markers can be efficiently localized. An alternative allocation would be using just one fluor for one chromosome, with multiple fluors to map an exponential number of IPM encoded DNA probes on that chromosome.

A procedure of many possible procedures is now given for constructing maps, identifying disease genes and using such disease genes.

Isolate and purify the DNA from a chromosome, whole genome, or portion thereof.

Form the DNA reagents from said genome for constructing map:

(1) DNA point reagents. These include STSs (e.g., microsatellite repeats used for genetic mapping), and other small DNA inserts.

(2) DNA probe reagents. These are comprised of genomic inserts contained within cosmid, P1, or YAC vectors.

(3) DNA covering region reagents. These include radiation hybrids, and pools of genomic clones, e.g., YACs.

Form Table A by comparing the DNA probe reagents against the DNA covering region reagents. This can be done by the steps of:

Extracting the DNA from the probe reagents. For species-specific DNA amplification, interspersed repetitive sequence (IRS) PCR can be performed.

Preparing gridded filters of the probe DNA reagents.

Extracting labelled DNA from the covering region reagents. This can be done using labelled PCR primers. For species-specific DNA amplification, use IRS-PCR.

Hybridizing the labelled DNA product of each covering region reagent against one or more gridded filters that contain the entire probe library. Cot1 DNA can be used to block repetitive sequences. This detects the intersection or overlap of the probes against the covering regions.

Scoring the hybridization results, and recording them in a computer.

Alternatively, form Table A as above, but transpose the DNA reagents by instead putting the covering region DNA onto gridded filters, labelling the probe DNA, and then conducting the hybridizations.

Form Table B by comparing the DNA covering region reagents against the DNA point reagents. This can be done by the steps of:

Preparing PCR primers corresponding to the STS point reagents.

Extracting the DNA from the covering region reagents. IRS-PCR need not be used here.

Preparing gridded filters of the covering region DNA reagents.

Performing labelled-PCR with each STS point reagent's PCR primers against one or more gridded filters that contain the entire covering region library. This detects the presence or absence of a point within a covering region.

Scoring the PCR amplification results, and recording them in a computer.

Alternatively, form Table B as above, but transpose the DNA reagents by instead testing each covering regions's DNA against an array of STSs using labelled STS primers in a multiplexed PCR reaction.

Forming Table L by combining Tables A and B using Inner Product Mapping.

Constructing a map of the DNA reagents. This is done by using Table L, and, possibly, iteratively using a global search mechanism (e.g., simulated annealing), together with search heuristics for permuting the rows and columns of Table L into the known shape of the desired solution. The final permutations determine the locations (i.e., both order and position, up to the desired map resolution) on the map of the DNA reagents.

Using said map, together with the well-known technique of positional cloning (also termed "reverse genetics"), to clone disease genes. This can be done in several ways. Each approach meets the three requirements for the cloning of a disease gene:

(a) genetic inheritance in affected family, (b) functional expression in affected tissues, and (c) localization on a genetic/physical map.

Four illustrative (out of many possible) approaches are presented. In these (and virtually all possible) approaches, the use of said map is crucial to enablement.

Approach 1.
Proceed directly from the constructed map.

(1) Establish phenotypic criteria for affected individuals.

(2) Identify and characterize families with affected individuals.

(3) Use said constructed map to perform genotyping and linkage analyses of said families to map the disease to a map location. Selection of the genetic markers may be random (their selection would be based on the optimal distribution along the genetic map) or based upon proximity to suspected DNA breakpoints (based upon cytogenetic cases), or related to known candidate genes (directly using the information of the physical map to select informative markers near specific genes).

(4) Use said constructed map to look up the corresponding physical DNA sequences corresponding to the map location.

(5) Use standard laboratory-based techniques on said physical DNA sequences to:

(5a) Find gene regions via promoter sequences. This can be done using rare restriction cutters to identify CpG-rich sequences.

(5b) Find gene regions via species conservation.

(5c) Clone candidate genes from these selected sequences.

(6) As an alternative to Step (5), sequence all said physical DNA sequences, and use standard computer-based techniques to:

(6a) Find gene regions by searching the sequences containing promoter and/or coding regions.

(6b) Find gene regions via species conservation. This can be done by comparing the sequences against sequence databases.

(6c) Clone candidate genes, say by direct DNA synthesis of these selected sequences.

(7) Express the candidate gene as messenger RNA (mRNA). Compare the expression of the mRNA (or its protein products) in appropriate tissues of affected and unaffected individuals to determine which candidate gene correlates with disease activity. The one which correlates is the disease gene.

Approach 2.
Proceed directly from the constructed map, but also use candidate genes derived from affected tissues.

(8) Proceed as in Steps 1–6.

(9) Obtain candidate genes derived from appropriate tissues of affected and unaffected individuals. Said candidate genes can be constructed by building cDNAs from the expressed mRNA. Compare the expressed candidate genes with the map-derived candidate genes, and find the disease gene by confirming identity.

Approach 3.
Proceed directly from candidate genes derived from affected tissues, but also use the constructed map.

(10) Construct candidate genes derived from appropriate tissues of affected and unaffected individuals. Said candidate genes can be constructed by building cDNAs from expressed mRNA in said tissues.

(11) Compare said expressed candidate genes with the physical DNA reagents (or their derivatives) that comprise the physical sequence component of said constructed genetic/physical map. This will determine the map location of said candidate gene on the map.

(12) Select genetic markers directly from the map. Alternatively, new markers can be constructed from the physical sequences or from the candidate gene DNA. A set of highly polymorphic genetic markers works best; since this is most likely not present on the candidate gene, use of the map is required to select or construct said polymorphic markers.

(13) Establish criteria for phenotypic expression in affected individuals.

(14) Identify families having affected individuals who express the disease.

(15) Use the said constructed genetic/physical map to verify that the phenotypic disease, and the candidate gene markers (derived using the map), both map to the same location. This confirms that the candidate gene is, in fact, the disease gene.

Approach 4.

A combined positional and candidate gene cloning strategy using the constructed map.

(16) Proceed as in Steps 1–3.

(17) Using the map, localize the disease-related gene between two flanking markers, or demonstrate linkage with one or more candidate genes. (Direct testing of a candidate gene, independently of linkage, would not require the use of the physical map. This situation would be the exception rather than the rule, since it is unusual for a specific candidate gene to be clearly established for a given disease.)

(18) If a specific candidate gene is identified by linkage analysis then one would proceed to step 19. If a specific candidate gene has not been strongly linked, or one or more of the initial candidate genes have been excluded by the criteria stated below, then one must identify additional candidate genes within the flanking genetic markers.

(18a) Potential candidate genes include those that have been previously localized to the region on the said physical map.

(18b) Additional candidate genes, which have not been previously identified and mapped would be identified by using the genomic contigs on the physical map corresponding to the region within the flanking markers to identify other potential genes either by sequence analysis (i.e., algorithms designed to identify regions of genomic DNA that are likely to encode genes or transcribed regions), or by experimental criteria including but not limited to CpG islands, exon trapping, cross-species conservation, and hybridization to specific clones from a suitable cDNA library. The experimental screening of the genomic region for candidate genes would generally include the use of expressed sequences from tissues that are thought to be affected by the disease.

(19) Specific candidate genes would be tested by mutation analysis, including but not limited to, alteration of genomic structure by insertion, deletion, or rearrangement, alteration of transcript size or abundance, loss of protein product or enzymatic function, point mutation detection by indirect (SSCP, DGGE, chemical cleavage, etc.) or direct methods (DNA sequencing, dideoxy-fingerprinting, ASO, etc.).

(20) Confirmation of the candidate gene by linkage analysis of the suspected mutation, and demonstration that the mutation is not present in the normal population. Additional functional studies may be employed to demonstrate that the particular mutation alters the normal function or structure of the geneo

(21) Perpetuation. The identified disease gene can be perpetuated by inserting the DNA sequence of the disease gene into a vector clone. Suitable vector clones are readily available either by purchase from any of a number of vendors, or by direct construction using well-known recombinant DNA techniques. With *E. coli*, for example, the insert DNA is maintained as a plasmid.

(22) Amplification. Following Step 21, the disease gene can be amplified by permitting the vector (e.g., *E. coli*) to grow to the desired quantity.

(23) Purification. There are dozens of established techniques for this step. With *E. coli* vectors, one approach would be to first disrupt the cell integrity, and the precipitate out the DNA component with salts. The plasmid DNA is then isolated by ultracentrifugation with a cesium chloride gradient, and then retrieving the plasmids from the appropriate band in the layered centrifuged product. Further plasmid-specific isolation may also be performed.

(25) Protein products. Expression systems are used to produce recombinant proteins. The most popular expression systems are the bacteria *E. coli*, and Bacillus subtilis, yeast, and cultured insect and mammalian cells. These exploit the transcriptional (DNA to mRNA) and translational (mRNA to protein) machinery of the intact cell to manufacture protein products. These protein products are then isolated and purified from this amplification procedure using well-known techniques, including ionic, column, electrophoretic, and centrifuge separations.

(24) DNA-based diagnostic tests. DNA-based diagnostic tests can be derived directly from the sequence of the isolated disease gene.

(24a) ASOs are developed from mutations in the exon region of the gene, which can then be detected using hybridization, SSCP, LCR, RFLP, or any other appropriate mutation assay.

(24b) Linkage markers are developed from polymorphic tandem repeat regions in the intron region of the gene, which can then be detected using differential sizing, hybridization, SSCP, RFLP, or any other appropriate mutation assay.

(24c) Direct sequencing of the DNA will identify allelic variations.

(24c) To use the diagnostic tests described in Steps 24*a*, 24*b*, and 24*c*, the disease gene region is amplified from an individual's blood using PCR (with labelled primers). The DNA-based diagnostic test is then applied to this DNA product to determine the individual's alleles. With linkage analysis, additional testing of family members may be required.

(25) Protein-based diagnostic tests. The protein product produced from the gene's DNA can also form the basis of a diagnostic test. This is done by sampling an individual's blood, and assaying for protein mutations. There are very many such specific assays, including immunodetection, specific binding assays, functional assays, and electrophoretic migration assays.

More generally, the inventive procedure involves:

Identifying a physical space which is to be mapped.

Setting a desired resolution of the map.

Isolating a sufficiently large set of sample points to achieve this desired resolution, each component sample point representative of a point which physically resides within the space and has a corresponding mass localized to a first volume within a predetermined range of the space.

Isolating a set of probes, probe representative of a probe which physically resides within the space and has a corresponding mass localized within a second volume of a predetermined range, said predetermined range of said second volume is greater than or equal to said predetermined range of said first volume.

Isolating a sufficiently large set of covering regions to achieve the desired resolution, each component covering region representative of a region which is comprised of a set of subregions each of which has an associated mass; the mass of each subregion extends over a connected volume that physically resides within the space and has a corresponding mass localized within a third volume of a predetermined range, said predetermined range of said third volume is greater than or equal to said predetermined range of said second volume. The total volume of said covering region [which does not exceed the total volume of its subregions] has a corresponding mass localized within a fourth volume of a predetermined range; said predetermined range of said fourth volume is sufficiently large to be within several orders of magnitude of the volume of the entire space.

In constructing the map, the three reagents are described by their relative sizes. Specifically, the size range (i.e., lengths) of the DNA sequences of the points, lines, and subregions of the covering regions must generally maintain the following relationship: range(point sequence)<range(line sequence)<range(subregion sequence).

For example, with a map constructed from STS points, YAC lines, and RH covering regions, one satisfies this inequality since:

range(STS sequence)=[100B, 500B], range(YAC sequence)=[100KB, 2000KB], range(RH fragment sequence)=[5MB, 50MB], where B denotes DNA base units, KB denotes kilobases, and MB denotes megabases. The IPM will also tolerate some deviation from this strict inequality relation.

The following measurements are physically realizable within this method:

Direct comparison measurement of containment or overlap of a probe against a covering region. A positive comparison indicates containment or overlap, a negative comparison indicates no containment or overlap, and an intermediate value indicates partial containment or overlap. The method accommodates uncertain comparison results, as well as false negative or false positive results.

Direct comparison measurement of containment or overlap of a covering region against a sample point. A positive comparison indicates containment or overlap, a negative comparison indicates no containment or overlap, and an intermediate value indicates partial containment or overlap. The method accommodates uncertain comparison results, as well as false negative or false positive results.

Using the physically realizable measurement procedures, two separate data tables are then acquired. For efficiency, this acquisition is best done in parallel manner, obtaining one row or column (or portions thereof) at a time. Specifically:

Table A which determines the containment or overlap of the probes against the covering regions.

Table B is obtained, which determines the containment or overlap of the sample points against the covering regions.

A combination to obtain Table L from Tables A and B, which provides localizing information about the probes relative to the sample points. One mechanism for determining Table L is by combining Tables A and B using any form of inner product combination. Typical inner product operations might include Boolean, arithmetic, or thresholding procedures.

A localization of the volumes of the sample points within the space. When the location or ordering of the sample points is not known, computation of Table L, together with a global search procedure such as simulated annealing, is used to localize the sample points. This is done by repeatedly permuting the columns of Table L (equivalently, the columns of Table B) to best cluster the densities in every row of Table L. Permutations may additionally be performed upon the rows of Table L (equivalently, the rows of Table A) to cluster the densities along the diagonal of Table L. Clustering measures on Table L may include operations for finding, grouping, and separating relatively larger or smaller values, preserving continuity, and fitting to predetermined functional forms.

A postprocessing of Table L to construct a map. This postprocessing step may be effected by any manner of curve fitting mechanisms, or the use of curve statistics derived therefrom. (Typical statistics include the location of relatively larger or smaller values, and estimates of variance.) Specifically, within said desired resolution, the map construction constructs a map which determines:

the location of the sample point volumes within the space, the location of the probe volumes within the space, relative to said sample point volumes, and, if so desired, the location of the covering region volumes within the space, relative to said sample point volumes.

All probes that are physically obtained using, at least in part, said map or localization process.

The purified derivatives of said physically obtained probes.

All useful applications of said physically obtained probes or their purified derivatives.

The probes can be clones containing nucleic acid inserts of any size, the sample points are small nucleic acid sequences such as STSs, and the covering regions are radiation hybrids or pooled nucleic acid fragments. Further, all these reagents are derived from the same chromosome or genome.

The probes can be clones containing nucleic acid inserts of any size, the covering regions are radiation hybrids or pooled nucleic acid fragments, and the rows of Table B are obtained by fluorescent in situ hybridization of the radiation hybrids' nucleic acid content against the genome. That is, the sample points are locations along the fluorescently derived radiation hybrid characterizations. Further, all these reagents are derived from the same chromosome or genome.

Alternatively, only Table B (the comparison of radiation hybrids against STSs) is obtained. Table A is then set equal to the transpose of Table B, i.e., the probes are themselves the STSs. The resulting map then localizes both the STSs and the radiation hybrid fragments.

Or, it can be for constructing ordered probe maps, wherein only Table A (the comparison of DNA sequence probes against radiation hybrids) is obtained. Table B is then set equal to the transpose of Table A. The product matrix L is then a symmetric matrix which compares each probe with every other probe. Each entry in L is the inner product of the radiation hybrid signatures of two probes. The resulting map then localizes the probes, without the need for STS reagents nor with comparisons of the radiation hybrids against STSs.

In another embodiment, the probes can be phenotypically observable traits or genes, the sample points are a dense (possibly ordered) array of genetic markers (such as STSs), and the covering regions are comprised of each individual's recombinant chromosomes, with the subregions thereof given by the chromosomal portions inherited from the founder(s) possessing the disease gene. Then, using identityby-descent or identity-by-state allele comparisons, the IPM-based superposition of the genetic marker alleles, with backprojection onto the alleles of the founder(s) possessing the disease chromosomes, will localize (i.e., map) the traits or genes.

In yet another embodiment, the present invention can be for constructing two or three dimensional maps of chromosomes, nucleic acid reagents (e.g., radiation hybrids) visualized on chromosomes, or other cellular organelles using fluorescent light microscopy. Each covering region corresponds to a fluorescent probe. Table A is the combinatorial encoding of each chromosome in terms of the fluorescent probes that represent it, and each row of Table B is a two or three dimensional microscopic image of the cell taken through a filter that selectively highlights one fluorescent probe. The inner product L of Tables A and B, taken across the common covering region dimension, extracts the spatial position of each chromosome.

Preferably, this method can be for constructing radiation hybrid maps, wherein only Table B (the comparison of hybrids against STSs) is obtained. Table A is then set equal to the transpose of Table B, i.e., the probes are themselves the STSs. The resulting map then localizes both the STSs and the radiation hybrid fragments. Or, it can be for constructing ordered probe maps, wherein only Table A (the comparison of DNA sequence probes against radiation hybrids) is obtained. Table B is then set equal to the transpose of Table A. The product matrix L is then a symmetric matrix which compares each probe with every other probe.

Each entry in L is the inner product of the radiation hybrid signatures of two probes. The resulting map then localizes the probes, without the need for STS reagents nor with comparisons of the radiation hybrids against STSs.

An apparatus for constructing maps comprises:

A computer, a memory, and data transfer devices.

A space to be mapped needs a desired resolution to be set out and useful physical reagents. Specifically:

A physical space which is to be mapped is identified.

A predetermined resolution of the resulting map.

A sufficiently large set of sample points to achieve this desired resolution, wherein each component sample point physically resides within the space and has a corresponding mass localized to a first volume within a predetermined range.

A set of probes, wherein each component probe physically resides within the space and has a corresponding mass localized within a second volume of a predetermined range. Specifically, said predetermined range of said second volume is greater than or equal to said predetermined range of said first volume.

A sufficiently large set of covering regions to achieve the desired resolution, wherein each component covering region is comprised of a set of subregions. The mass of each subregion extends over a connected volume that physically resides within the space and has a corresponding mass localized within a third volume of a predetermined range. Specifically, said predetermined range of said third volume is greater than or equal to said predetermined range of said second volume. The total volume of said covering region (which does not exceed the total volume of its subregions) has a corresponding mass localized within a fourth volume of a predetermined range; said predetermined range of said fourth volume is sufficiently large to be within several orders of magnitude of the volume of the entire space.

Physically realizable measurements, specifically:

Direct comparison measurement of containment or overlap of a probe against a covering region. A positive comparison indicates containment or overlap, a negative comparison indicates no containment or overlap, and an intermediate value indicates partial containment or overlap. The method accommodates uncertain comparison results, as well as false negative or false positive results.

Direct comparison measurement of containment or overlap of a covering region against a sample point. A positive comparison indicates containment or overlap, a negative comparison indicates no containment or overlap, and an intermediate value indicates partial containment or overlap. The method accommodates uncertain comparison results, as well as false negative or false positive results.

Data buffers which may contain three data tables, A, B, and L. Specifically:

Table A, which contains the containment or overlap of the probes against the covering regions, Table B, which contains the containment or overlap of the sample points against the covering regions, and Table L, which is a combination of Tables A and B.

A first program resident in the memory component, which can compute a combination of Tables A and B to produce a localization Table L. The particular combination operation may be comprised of an inner product combination, which can entail Boolean, arithmetic, and/or thresholding procedures. Further processing of the rows of Table L may include curve fitting mechanisms for determining curve statistics, such as the location of maxima or minima.

A second program resident in the memory component, which can compute a localization of the volumes of the sample points within the space. Specifically, when the location or ordering of the sample points is not known, said second program can localize the sample points by using said program 1, together with a global search procedure such as simulated annealing, and thereby localize the sample points. This is done by repeatedly permuting the columns of Table L (equivalently, the columns of Table B) to best cluster the densities in every row of Table L. Permutations may additionally be performed upon the rows of Table L (equivalently, the rows of Table A) to cluster the densities along the diagonal of Table L. Clustering measures on Table L may include operations for finding, grouping, and separating relatively larger or smaller values, preserving continuity, and fitting to predetermined functional forms.

A postprocessing computation of Table L to construct a map. This postprocessing step may be effected by any manner of curve fitting mechanisms, or the use of curve statistics derived therefrom. (Typical statistics include the location of relatively larger or smaller values, and estimates of variance.) Specifically, within said desired resolution, the map construction determines:

the location of the sample point volumes within the space, the location of the probe volumes within the space, relative to said sample point volumes, and, if so desired, the location of the covering region volumes within the space, relative to said sample point volumes.

An optional output data buffer for containing the map formed by said postprocessing computation of Table L.

From the map, probes can be obtained.

The means of effecting the said combination of Tables A and B can be by means of an inner product operation. Said inner product operation may include matrix multiplication, graph processing, set manipulation, list processing, vector processing, or any other formulation or data representation that is mathematically equivalent to performing any step of inner product operation.

Preferably, any of the matrices A, B, or L can be determined, provided that the other two are known. This holds, for example, when the inner product operation is the usual matrix multiplication "sum over product", and arithmetic values (say, −1 to +1) are used in the matrices. The determination of matrices A or B is effected by standard or least squares matrix inversion. This may be useful, for example, in ascertaining probe or sample point signatures.

Such an apparatus can also include:

A simulation module that can generate IPM test examples according to different experimental reagents and conditions.

A mapping module that can solve problems using IPM and construct maps.

An analysis module that can assess the utility of IPM's solutions.

A visualization module that can present IPM's results and analyses in a visually perspicuous, and interactive, way.

Pattern recognition or pattern matching.

Machine learning application.

Clustering operations in one or more dimensions.

Neural or connectionist network learning procedure.

Neural or connectionist network operation.

Fuzzy logic application.

A system for constructing maps would utilize the following:

A physical space which is to be mapped.

A predetermined resolution of the resulting map.

A sufficiently large set of sample points to achieve this desired resolution, wherein each component sample point physically resides within the space and has a corresponding mass localized to a first volume within a predetermined range.

A set of probes, wherein each component probe physically resides within the space and has a corresponding mass localized within a second volume of a predetermined range. Specifically, said predetermined range of said second volume is greater than or equal to said predetermined range of said first volume.

A sufficiently large set of covering regions to achieve the desired resolution, wherein each component covering region is comprised of a set of subregions. The mass of each subregion extends over a connected volume that physically resides within the space and has a corresponding mass localized within a third volume of a predetermined range. Specifically, said predetermined range of said third volume is greater than or equal to said predetermined range of said second volume. The total volume of said covering region (which does not exceed the total volume of its subregions) has a corresponding mass localized within a fourth volume of a predetermined range; said predetermined range of said fourth volume is sufficiently large to be within several orders of magnitude of the volume of the entire space.

Physically realizable measurements, specifically:

Direct comparison measurement of containment or overlap of a probe against a covering region. A positive comparison indicates containment or overlap, a negative comparison indicates no containment or overlap, and an intermediate value indicates partial containment or overlap. The method accommodates uncertain comparison results, as well as false negative or false positive results.

Direct comparison measurement of containment or overlap of a covering region against a sample point. A positive comparison indicates containment or overlap, a negative comparison indicates no containment or overlap, and an intermediate value indicates partial containment or overlap. The method accommodates uncertain comparison results, as well as false negative or false positive results.

A parallel experimentation approach for efficiently acquiring two data tables. Specifically:

Table A, which contains the containment or overlap of the probes against the covering regions, and Table B, which contains the containment or overlap of the sample points against the covering regions.

An apparatus comprised of a computer, a memory, and data transfer devices that can combine Tables A and B to construct a map. This apparatus has input data buffers for Tables A and B, as well as an intermediate buffer for Table L. It contains one program resident in memory which forms the inner product Table L by combining Tables A and B. It may have a second program resident in memory which can use Table L, together with a global search procedure such as simulated annealing, to correctly localize the volumes of the sample points. Additional post-processing programs may be present in memory to effect the final probe localization, which constructs the map. The output of this apparatus is a map that integrates the locations of the volumes of the sample points, probes, and, possibly, the covering regions.

An integrated map of any resolution, comprised of the volumes of the sample points, the probes, and, possibly, the covering regions, which can be used to localize probes and sample points on the same map.

The physical probes obtained by retrieving a small subset of probes based on their location in the original or derived map. This map location may be based on proximity to one or more sample point locations.

The further purification or characterization of the physical construction of this small subset of physical probes.

All useful products and applications that can be derived from said physically characterized probes or their purified derivatives.

The probes can be clones containing nucleic acid inserts of any size, the sample points are small nucleic acid sequences such as STSs, and the covering regions are radiation hybrids or pooled nucleic acid fragments. Further, all these reagents are derived from the same chromosome or genome. Specifically, the system comprises:

A parallel experimentation approach for efficiently acquiring two data tables of the requisite genomic reagents.

An apparatus comprised of a computer, a memory, and data transfer devices that can perform the IPM operation for genome mapping.

The resulting integrated genome map of any resolution, comprised of the nucleic acid sample points, nucleic acid probes, and nucleic acid covering regions, which can be used to localize probes and sample points on the same map.

The physical probes (e.g., YACs, cosmids, phagemids, BACs, or STSs) obtained by retrieving a small subset of probes based on their location in the original or derived map. This map location may be based on proximity to one or more sample point (e.g., STS) locations, especially STS markers that are selected because of their association with a particular genetic trait or disease. The genetic association may be determined by genetic mapping studies in families that integrate the STS's genetic recombination distance with their physical distances on the integrated genome map.

The further characterization of the physical construction of this small subset of physical probes, such as the determination of their nucleic acid sequences.

All genes that are found to reside within these nucleic acid sequences. This specifically includes the gene (or genes) that causes the particular trait or disease.

All useful purified gene products, and applications of those purified gene products, that can be derived from said genes. Such products and applications include:

Nucleic acid markers obtained from within (or near) the gene, used, for example, as diagnostic tests for the particular trait or disease.

The protein (and its derivatives) that the gene codes for, used, for example, to better understand the mechanism of the particular trait or disease.

Diagnostic and therapeutic mechanisms derived from either the gene (e.g., gene therapy), its protein (e.g., immunological diagnostics, or protein-derived pharmaceutical therapeutics), or the improved understanding of the mechanism of the particular trait or disease (e.g., indirect pharmaceutical agents).

Any form of such map construction can be used for:

(a) ordering probe reagents via ordered sample point reagents, (b) ordering sample point reagents via ordered probe reagents, (c) simultaneously ordering both sample point and probe reagents, (d) determining distances along said constructed maps, (e) constructing a map of sample point or probe reagents.

Covering regions can be characterized for the purpose of using Table B to construct maps by any of these reagents:

(a) Ordered sample points, obtained by any sample point ordering process based on covering regions.

(b) Fluorescent visualization of the covering regions.

(c) Unordered sample points, which are ordered by said map construction system in any manner.

A manufacturing process for constructing maps would utilize the following:

A physical space which is to be mapped.

A predetermined resolution of the resulting map.

A sufficiently large set of sample points to achieve this desired resolution, wherein each component sample point physically resides within the space and has a corresponding mass localized to a first volume within a predetermined range.

A set of probes, wherein each component probe physically resides within the space and has a corresponding mass localized within a second volume of a predetermined range. Specifically, said predetermined range of said second volume is greater than or equal to said predetermined range of said first volume.

A sufficiently large set of covering regions to achieve the desired resolution, wherein each component covering region is comprised of a set of subregions. The mass of each subregion extends over a connected volume that physically resides within the space and has a corresponding mass localized within a third volume of a predetermined range. Specifically, said predetermined range of said third volume is greater than or equal to said predetermined range of said second volume. The total volume of said covering region (which does not exceed the total volume of its subregions) has a corresponding mass localized within a fourth volume of a predetermined range; said predetermined range of said fourth volume is sufficiently large to be within several orders of magnitude of the volume of the entire space.

Physically realizable measurements, specifically:

Direct comparison measurement of containment or overlap of a probe against a covering region. A positive comparison indicates containment or overlap, a negative comparison indicates no containment or overlap, and an intermediate value indicates partial containment or overlap. The method accommodates uncertain comparison results, as well as false negative or false positive results.

Direct comparison measurement of containment or overlap of a covering region against a sample point. A positive comparison indicates containment or overlap, a negative comparison indicates no containment or overlap, and an intermediate value indicates partial containment or overlap. The method accommodates uncertain comparison results, as well as false negative or false positive results.

A highly parallel experimentation approach for very efficiently acquiring two data tables. Specifically:

Table A contains the containment or overlap of the probes against the covering regions, Table B contains the containment or overlap of the sample points against the covering regions.

Entire rows or columns (or portions thereof) of Table A can be determined in a single experiment. Entire rows or columns (or portions thereof) of Table B can be determined in a single experiment. Further, under suitable conditions, the number of covering regions is proportional to just the logarithm of the number of sample points. That is, the manufacturing process is designed to greatly reduce the acquisition cost of the data required for constructing a useful map.

An apparatus comprised of a computer, a memory, and data transfer devices that can combine Tables A and B to construct a map. This apparatus has input data buffers for Tables A and B, as well as an intermediate buffer for Table L. It contains one program resident in memory which forms the inner product Table L by combining Tables A and B. It may have a second program resident in memory which can use Table L, together with a global search procedure such as simulated annealing, to correctly localize the volumes of the sample points. Additional post-processing programs may be present in memory to effect the final probe localization, which constructs the map. The output of this apparatus is a map that integrates the locations of the volumes of the sample points, probes, and, possibly, the covering regions.

Applying the apparatus to the data tables constructs an integrated map of any resolution, comprised of the volumes of the sample points, probes, and covering regions, which can be used to localize probes and sample points on the same map.

The physical probes obtained by retrieving a small subset of probes based on their location in the original or derived map. This map location may be based on proximity to one or more sample point locations.

The further purification or characterization of the physical construction of this small subset of physical probes.

All useful products and applications that can be derived from said physically characterized probes or their purified derivatives.

The probes can be clones containing nucleic acid inserts of any size, the sample points are small nucleic acid sequences such as STSs, and the covering regions are radiation hybrids or pooled nucleic acid fragments. Further, all these reagents are derived from the same chromosome or genome. Genetic mapping studies in families can integrate the STS's genetic recombination distance with their physical distances on the integrated genome map. Specifically, the output of the manufacturing process is an integrated genetic/physical map comprised of genetically useful markers (e.g., STSs) and of reagents (e.g., cosmids) or indices to (e.g., YACs) sequence-ready nucleic acid insert clones.

The manufacturing process can be for identifying probes of interest that are located near sample points of interest comprising:

An integrated map that localizes both probes and sample points.

Using this integrated map to spatially identify localized probes by their neighboring sample points. The physical probes are obtained by retrieving a small subset of probes based on their location in the original or derived map. This map location may be based on proximity to one or more sample point locations.

Further characterizing the physical construction of each of these physical probes.

Developing useful products and applications that are derived from these characterized probes and their derivatives.

Preferably, the manufacturing process can be for identifying nucleic acid probes of interest, the genes residing on these probes, and their useful applications, that are located near nucleic acid sample points of interest comprising:

The integrated genetic/physical map that localizes both probes and sample points.

Physical probes (e.g., YACs, cosmids, phagemids, BACs, or STSs) are obtained by retrieving one or more probes based on their map location. This map location may be based on proximity to one or more sample point (e.g., STS) locations, selected as genetic markers that are associated with a particular genetic trait or disease.

The further characterization of these physical probes, effected, in part, by determining their nucleic acid sequences.

Genes that are found within these nucleic acid sequences by scanning for open coding regions. Such genes specifically includes the gene (or genes) that causes the particular trait or disease. Purified gene products, and useful applications of those purified gene products, can then be derived from said genes. Such products and applications that are obtainable from this manufacturing process include:

Nucleic acid markers obtained from within (or near) the gene, used, for example, as diagnostic tests for the particular trait or disease.

The protein (and its derivatives) that the gene codes for, used, for example, to better understand the mechanism of the particular trait or disease.

Diagnostic and therapeutic mechanisms derived from either the gene (e.g., gene therapy), its protein (e.g., immunological diagnostics, or protein-derived pharmaceutical therapeutics), or the improved understanding of the mechanism of the particular trait or disease (e.g., indirect pharmaceutical agents).

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for cloning a gene of a genome comprising the steps of:

isolating a set of first nucleic acid fragments, each first fragment part of the genome;

isolating a set of second nucleic acid fragments, each second fragment part of the genome;

isolating a set of collections of third nucleic acid fragments, each collection including a third fragment that is part of the genome and that has a size greater than or equal to the average size of said second fragments;

forming a Table A, wherein each row (or column) of Table A consists of the results of a determination of which collections of third fragments hybridize with a specific second fragment;

forming a Table B, wherein each column (or row) of Table B consists of the results of a determination of which collections of third fragments contain the sequence of a specific first fragment;

determining a map location of each second fragment by forming a comparison between Table A and Table B, wherein the comparison finds which column (or row) of Table B most closely matches the row (or column) of Table A corresponding to the given second fragment: producing a map which determines where the first fragments are located within the genome and where the second fragments are located within the genome; and isolating the gene by positional cloning using the map.

2. A method as described in claim 1 wherein the first fragments are STSs, genetic markers or genes, the second fragments are genome fragments cloned in YACs or bacteria, and the collections of third fragments are radiation hybrids or pools of genome fragments.

3. A genome mapping method comprising the steps of:

isolating a set of first nucleic acid fragments, each first fragment part of the genome;

isolating a set of second nucleic acid fragments, each second fragment part of the genome;

isolating a set of collections of third nucleic acid fragments, each collection including a third fragment that is part of the genome and that has a size greater than or equal to the average size of said second fragments;

forming a Table A, wherein each row (or column) of Table A consists of the results of a determination of which collections of third fragments hybridize with a specific second fragment;

forming a Table B, wherein each column (or row) of Table B consists of the results of a determination of which collections of third fragments contain the sequence of a specific first fragment; and determining a man location of each second fragment by forming a comparison between Table A and Table B, wherein the comparison finds which column (or row) of Table B most closely matches the row (or column) of Table A corresponding to the given second fragment.

4. The method as described in claim 3 further comprising the step of sequencing an element in the set of second fragments, thereby determining the DNA sequence of said element.

5. The method as described in claim 3 further comprising the step of isolating a gene by positional cloning using said map.

6. The method as described in claim 3 further comprising the steps of:

obtaining nucleic acid materials from the genomes of a first set of individuals expressing a trait, and of a second set of individuals whose members are biologically related to a member of the first set of individuals;

identifying and isolating a gene linked to said trait by positional cloning;

determining the DNA sequence of the gene;

analyzing mutations in the genome of the first and second sets of individuals to produce mutation data;

verifying that the gene is causative or tightly linked to the trait using said mutation data; and purifying the gene.

7. The method as described in claim 3 wherein the step of forming a Table A includes the step of forming nucleic acid hybridization comparisons.

8. The method as described in claim 3 wherein the step of forming a Table A includes the step of forming nucleic acid hybridization comparisons, and the hybridization probes of the nucleic acid hybridization comparison step include collections of third fragments.

9. The method as described in claim 3 wherein the step of forming a Table A includes the step of forming nucleic acid hybridization comparisons, the hybridization probes of the nucleic acid hybridization comparison step include collections of third fragments, and the third fragments may be mixed with nucleic acid from a species different from that of the genome to be mapped.

10. The method as described in claim 3 wherein the step of forming a Table A includes the step of forming nucleic acid hybridization comparisons, the hybridization probes of the nucleic acid hybridization comparison step include collections of third fragments, and the collections of third fragments include nucleic acid material from radiation hybrids.

11. The method as described in claim 3 wherein the step of forming a Table A includes the step of forming nucleic acid hybridization comparisons, the hybridization probes of the nucleic acid hybridization comparison step include collections of third fragments, and the collections of third fragments include nucleic acid material from a plurality of genomic insert clones.

12. The method as described in claim 3 wherein there is a desired resolution of the map, and the step of determining a map location of each second fragment by forming comparisons between Table A and Table B is performed with the data in Table A alone or in Table B alone insufficient to achieve the desired resolution.

13. The method as described in claim 3 wherein the sum of the sizes of the second fragments is greater than or equal to the size of the portion of the genome to be mapped.

14. The method as described in claim 3 wherein the first set of fragments includes polymorphic genetic markers useful for positional cloning.

15. The method as described in claim 3 wherein the step of determining a map location of each second fragment by forming comparisons between Table A and Table B includes the step of producing a map from data in Table A or Table B that includes false negative or false positive results.

16. The method as described in claim 3 wherein following the step of determining a map location of each second fragment by forming comparisons between Table A and Table B, there is the step of determining where the first fragments are located within the genome and where the second fragments are located within the genome.

17. The method as described in claim 3 wherein the the column (or row) of Table B that best matches the row (or column) of Table A corresponding to the given second fragment does not exactly match the row (or column) of Table A corresponding to the given second fragment.

18. The method as described in claim 3 wherein the step of determining a map location of each second fragment by forming comparisons between Table A and Table B includes the step of producing a map that positions at least 25 of the second fragments within 2.8 Mb of their true location on the portion of the genome.

19. The method as described in claim 3 wherein the step of determining a map location of each second fragment by forming comparisons between Table A and Table B includes the step of producing a location of a second fragment using only that data in Table A which pertains to said second fragment.

20. The method as described in claim 3 wherein the number of collections of third fragments is logarithmically related to the desired resolution.

21. The method as described in claim 3 wherein the Table B results describe the locations of the third fragments along the genome.

22. The method as described in claim 3 wherein the step of forming a Table A includes a determination using a fragment amplified by a polymerase chain reaction.

23. The method as described in claim 3 wherein the step of forming a Table A includes a determination using a fragment labeled by a detectable label.

24. The method as described in claim 3 wherein the step of determining a map location of each second fragment includes an inner product comparison to find the closest match.

25. The method as described in claim 3 wherein the step of forming Table A includes the step of forming Table A in a memory of a computer.

26. The method as described in claim 25 wherein the step of forming Table B includes the step of forming Table B in the memory of the computer.

27. The method as described in claim 26 wherein the step of determining a map location includes the step of operating a processor of the computer on Table A and Table B.

* * * * *